(12) United States Patent
Parvulescu et al.

(10) Patent No.: US 9,987,624 B2
(45) Date of Patent: Jun. 5, 2018

(54) TIN-CONTAINING ZEOLITIC MATERIAL HAVING AN MWW-TYPE FRAMEWORK STRUCTURE

(71) Applicant: BASF SE, Ludwigshafen (DE)

(72) Inventors: Andrei-Nicolae Parvulescu, Ruppertsberg (DE); Ulrich Müller, Neustadt (DE); Georg Uhl, Kaiserslautern (DE); Joaquim H. Teles, Waldsee (DE); Nicolas Vautravers, Mannheim (DE); Dominic Riedel, Lampertheim (DE)

(73) Assignee: BASF SE (DE)

( * ) Notice: Subject to any disclaimer, the term of this patent is extended or adjusted under 35 U.S.C. 154(b) by 84 days.

(21) Appl. No.: 15/033,402

(22) PCT Filed: Nov. 5, 2014

(86) PCT No.: PCT/EP2014/073809
§ 371 (c)(1),
(2) Date: Apr. 29, 2016

(87) PCT Pub. No.: WO2015/067655
PCT Pub. Date: May 14, 2015

(65) Prior Publication Data
US 2016/0256859 A1     Sep. 8, 2016

(30) Foreign Application Priority Data

Nov. 5, 2013   (EP) ..................................... 13191693

(51) Int. Cl.
*C01B 39/06*   (2006.01)
*C01B 39/48*   (2006.01)
(Continued)

(52) U.S. Cl.
CPC ......... *B01J 29/7088* (2013.01); *B01J 35/002* (2013.01); *B01J 35/1019* (2013.01); (Continued)

(58) Field of Classification Search
CPC ......... C01B 39/06; C01B 39/48; C01B 39/46; B01J 29/7088; B01J 37/30; B01J 2229/183; C07C 45/58
See application file for complete search history.

(56) References Cited

U.S. PATENT DOCUMENTS

| 7,326,401 | B2 | 2/2008 | Tatsumi et al. |
| 2005/0158238 | A1 | 7/2005 | Tatsumi et al. |
| 2016/0376159 | A1* | 12/2016 | Liu ....................... C01B 39/087 423/708 |

FOREIGN PATENT DOCUMENTS

| CN | 100522808 C | 8/2009 |
| CN | 102875491 A | 1/2013 |

(Continued)

OTHER PUBLICATIONS

Camblor, M., et al., "Synthesis and Structural Characterization MWW Type Zeolite ITQ-1, the Pure Silica Analog of MCM-22 and SSZ-25", J.Phys. Chem., 1998, vol. 102, pp. 44-51.

Liu, G., et al., "Hydrothermal synthesis of MWW-type stannosilicate and its post-structural transformation to MCM-56 analogue", Microporous and Mesoporous Materials, 2013, vol. 165, pp. 210-218.

(Continued)

*Primary Examiner* — David M Brunsman
(74) *Attorney, Agent, or Firm* — Drinker Biddle & Reath LLP

(57) ABSTRACT

A process for preparing a tin-containing zeolitic material having an MWW-type framework structure comprising providing a zeolitic material having an MWW-type framework structure having vacant tetrahedral framework sites, providing a tin-ion source in solid form, and incorporating tin into the zeolitic material via solid-state ion exchange.

29 Claims, 2 Drawing Sheets

(51) Int. Cl.
    *B01J 29/70*    (2006.01)
    *C01B 39/12*    (2006.01)
    *C07C 45/58*    (2006.01)
    *B01J 35/00*    (2006.01)
    *B01J 35/10*    (2006.01)
    *B01J 37/08*    (2006.01)
    *B01J 37/30*    (2006.01)
    *C01B 39/02*    (2006.01)
    *C01B 39/46*    (2006.01)

(52) U.S. Cl.
    CPC ............... *B01J 37/08* (2013.01); *B01J 37/30* (2013.01); *C01B 39/026* (2013.01); *C01B 39/06* (2013.01); *C01B 39/12* (2013.01); *C01B 39/46* (2013.01); *C07C 45/58* (2013.01); *B01J 2229/183* (2013.01); *C01B 39/48* (2013.01); *C07C 2601/10* (2017.05)

(56) References Cited

FOREIGN PATENT DOCUMENTS

WO    WO-03/074422 A1    9/2003
WO    WO-2013117537 A1   8/2013

OTHER PUBLICATIONS

Guo, Q., et al., "Highly Active and Recyclable Sn-MWW Zeolite Catalyst for Sugar Conversion to Methyl Lactate and Lactic Acid", ChemSusChem, vol. 6, No. 8, (2013), pp. 1352-1356.
International Search Report with Written Opinion of International Searching Authority for PCT/EP2014/073809 dated Feb. 2, 2015.
Chinese Office Action with English Translation for Chinese Application No. 201480060609.6, dated Jun. 2, 2017.
Hamond, C., et al., "Simple and Scalable Preparation of Highly Active Lewis Acidic Sn-β", Angew. Chem. Int. Ed., 2012, vol. 51, pp. 11736-11739.

* cited by examiner

US 9,987,624 B2

TIN-CONTAINING ZEOLITIC MATERIAL HAVING AN MWW-TYPE FRAMEWORK STRUCTURE

CROSS-REFERENCE TO RELATED APPLICATIONS

This application is a national stage application (under 35 U.S.C. § 371) of PCT/EP2014/073809, filed Nov. 5, 2014, which claims benefit of European Application No. 13191693.4, filed Nov. 5, 2013, both applications of which are incorporated herein by reference in their entirety.

The present invention is directed to a solid-state ion exchange process for preparing a tin-containing zeolitic material having an MWW-type framework structure. The inventive process comprises providing a zeolitic material having an MWW-type framework structure having vacant tetrahedral framework sites and further comprises providing a tin-ion source in solid form. In a solid-state ion exchange stage, tin is incorporated into the zeolitic material. Optionally, the resulting zeolitic material is calcined. In a post-treatment stage, the thus obtained calcined material can be treated with acidic aqueous solution.

BACKGROUND OF THE INVENTION

Zeolites are widely used in the chemical industry, for example as heterogeneous catalysts for various chemical and petrochemical processes. Therefore, providing zeolitic materials with novel and advantageous characteristics plays a crucial role in the development of catalysts, catalyst components, and catalyst support materials.

WO 03/074422 A1 and U.S. Pat. No. 7,326,401 B2 both describe a process for synthesizing a zeolite material having MWW structure. A tin-containing MWW is mentioned in the description, having a tin loading of about 4.7 weight-%. This tin-containing MWW is prepared from a B-MWW zeolite precursor which is deboronated by acid treatment before the Sn is introduced.

Furthermore, in Microporous and Mesoporous Materials 165 (2013), pages 210-218, the use of a tin-containing zeolitic material having an MWW framework structure in the BaeyerVilliger oxidation reaction of 2-adamantanone is described. According to this document, the zeolitic materials are obtained from a boron-containing precursor material which is not subjected to deboronation resulting in a material having a comparatively high boron content.

DETAILED DESCRIPTION OF THE INVENTION

Figure 1:
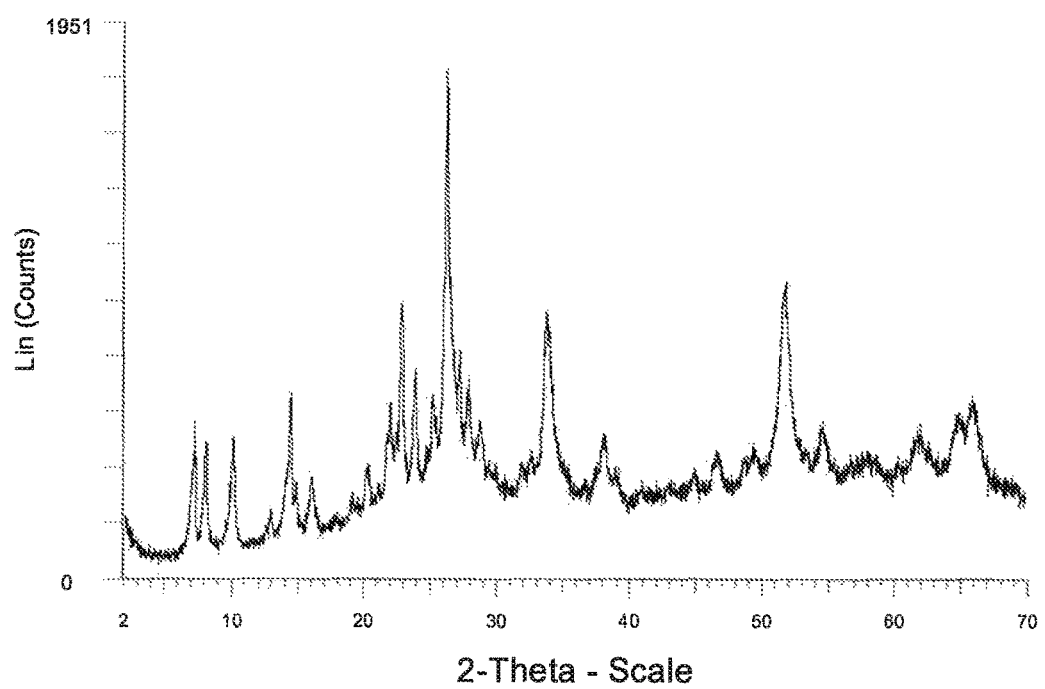
FIG. 1 is an X-ray diffraction (XRD) of a zeolite material with a MWW-Framework of the invention.

According to these prior art documents, tin-containing zeolites having an MWW-type framework structure are prepared by incorporation of tin into the zeolitic framework by hydrothermally treating a zeolitic material having an MWW-type framework structure and having vacant tetrahedral framework sites in the presence of tin-ion source. However, regarding this hydrothermal incorporation of tin, disadvantages have to be taken into account such as long synthesis time periods, the necessity to employ crystallization auxiliaries such as HF or cost intensive templating agents. Still further, only tin-containing zeolites having an MWW-type having a comparatively low tin content could be obtained.

Therefore, it was an object of the present invention to provide tin-containing zeolitic material having an MWW-type framework structure exhibiting improved characteristics if used as a catalytically active material, in particular if used as catalytically active material in oxidation reactions such as BaeyerVilliger-type oxidation like the BaeyerVilliger oxidation of cyclic ketones, or in isomerization reactions such as the isomerization of alpha-pinene oxide to campholenic aldehyde.

Thus, it was a further object of the invention to provide an improved process for the preparation of a tin-containing zeolitic material having an MWW-type framework structure comprising incorporating tin in an MWW-type framework structure having vacant tetrahedral sites.

Surprisingly, it was found that these objections can be achieved by preparing a zeolitic material having an MWW-type framework structure by incorporating tin in an MWW-type framework structure having vacant tetrahedral sites via a solid-state ion exchange stage.

Therefore, the present invention is directed to a process for preparing a tin-containing zeolitic material having an MWW-type framework structure comprising (i) providing a zeolitic material having an MWW-type framework structure comprising $X_2O_3$ and $YO_2$, wherein Y is a tetravalent element selected from the group consisting of Si, Ti, Zr, Ge, and combinations of two or more thereof, and X is a trivalent element selected from the group consisting of Al, B, In, Ga, Fe, and combinations of two or more thereof, said MWW-type framework structure having vacant tetrahedral framework sites;

(ii) providing a tin-ion source in solid form;

(iii) incorporating tin into the zeolitic material provided in (i) by bringing the zeolitic material provided in (i) in contact with the tin-ion source provided in (ii) under solid-state ion exchange conditions, obtaining a tin-containing zeolitic material having an MWW-type framework structure.

According to the present invention, it was found that it was possible to prepare a tin-containing zeolitic material having an MWW-type framework structure by incorporating tin in an MWW-type framework structure having vacant tetrahedral sites via a solid-state ion exchange stage. Further, it was found that this novel method for preparing a tin-containing zeolitic material having an MWW-type framework structure is not only a very simple process compared to the hydrothermal synthesis process of the prior art, but is also a process which allows preparing tin-containing zeolitic material having an MWW-type framework structure having a higher tin content compared to the processes of the prior art, which novel tin-containing zeolitic material having an MWW-type framework structure exhibit better characteristics if, for example, used in oxidation reactions or isomerization reactions.

Step (i)

According to step (i) of the process of the present invention, a zeolitic material is provided having an MWW-type framework structure comprising $X_2O_3$ and $YO_2$, wherein Y is a tetravalent element selected from the group consisting of Si, Ti, Zr, Ge, and combinations of two or more thereof, and X is a trivalent element selected from the group consisting of Al, B, In, Ga, Fe, and combinations of two or more thereof, said MWW-type framework structure having vacant tetrahedral framework sites.

The term "MWW-type framework structure" as used in the context of the present invention relates to those zeolitic materials having the MWW structure type which is defined, for example, in Camblor et al. and also those zeolitic structures which are derived from this structure and have a different interlayer distance, indicated by a different lattice parameter c. Preferably, a tin-containing zeolitic material according to the present invention has an X-ray diffraction pattern comprising peaks at 2 theta diffraction angles of $(7.1\pm0.1)°$, and $(7.9\pm0.1)°$, more preferably an X-ray diffraction pattern comprising peaks at 2 theta diffraction angles of $(7.1\pm0.1)°$, $(7.9\pm0.1)°$, $(9.6\pm0.1)°$, $(12.8\pm0.1)°$, $(14.4\pm0.1)°$, $(14.7\pm0.1)°$, $(15.8\pm0.1)°$, $(19.3\pm0.1)°$, $(20.1\pm0.1)°$, $(21.7\pm0.1)°$, $(21.9\pm0.1)°$, $(22.6\pm0.1)°$, $(22.9\pm0.1)°$, $(23.6\pm0.1)°$, $(25.1\pm0.1)°$, $(26.1\pm0.1)°$, $(26.9\pm0.1)°$, $(28.6\pm0.1)°$, and $(29.1\pm0.1)°$.

Preferably, the tetravalent element Y is Si. Therefore, the present invention relates to a process wherein according to (i), a zeolitic material is provided having an MWW-type framework structure comprising $X_2O_3$ and $YO_2$, wherein Y is Si and X is a trivalent element selected from the group consisting of Al, B, In, Ga, Fe, and combinations of two or more thereof, said an MWW-type framework structure having vacant tetrahedral framework sites.

Preferably, the trivalent element X is B. Therefore, the present invention relates to a process wherein according to (i), a zeolitic material is provided having an MWW-type framework structure comprising $X_2O_3$ and $YO_2$, wherein Y is a tetravalent element selected from the group consisting of Si, Ti, Zr, Ge, and combinations of two or more thereof, and X is B, said an MWW-type framework structure having vacant tetrahedral framework sites.

More preferably, the tetravalent element Y is Si and the trivalent element X is B. Therefore, the present invention relates to a process wherein according to (i), a zeolitic material is provided having an MWW-type framework structure comprising $X_2O_3$ and $YO_2$, wherein Y is Si and wherein X is B.

Generally, no specific restrictions exist how this zeolitic material having vacant tetrahedral sites is provided. For example, it is conceivable to purchase a suitable, commercially available zeolitic material having vacant tetrahedral sites. Further, for example, any conceivable process for preparing such a zeolitic material can be employed for providing the zeolitic material. For example, it is conceivable to suitably synthesize a zeolitic material having an MWW-type framework structure as a starting zeolitic material from suitable sources of $X_2O_3$ and $YO_2$, either in the presence or in the absence of a suitable template compound, with or without making use of suitable seed crystals, for example in a hydrothermal synthesis process, and subject said starting zeolitic material, after optional washing and/or drying and/or calcining, to a suitable process stage wherein at least a portion of X is removed from the zeolitic framework and the vacant tetrahedral sites are formed. For example, at least a portion of X can be removed from the zeolitic framework by a treatment with steam and/or by a treatment with an acid. In the context of the present invention, it was found that in particular if X is B, the zeolitic framework having the vacant tetrahedral sites which is used for the subsequent solid-state ion exchange process is advantageously prepared by removing X from the zeolitic framework in a very mild process wherein neither steam nor an acid is used. In particular, it was found that X, preferably B, can be removed by treating the zeolitic starting material with a liquid solvent system, preferably under reflux, wherein the liquid solvent system is preferably selected from the group consisting of water, methanol, ethanol, propanol, ethane-1,2-diol, propane-1,2-diol, propane-1,3-diol, propane-1,2,3-triol, and mixtures of two or more thereof, the liquid solvent system more preferably being water, wherein more preferably, the liquid solvent system does not contain an inorganic or organic acid, or a salt thereof, and wherein the treating is preferably carried out at a temperature in the range of from 50 to 125° C., more preferably from 90 to 115° C., more preferably from 95 to 105° C., and preferably for a period in the range of from 6 to 20 h, more preferably from 7 to 17 h, more preferably from 8 to 12 h.

Preferably, according to (i) the zeolitic material having an MWW-type framework structure having vacant tetrahedral framework sites is provided by a method comprising (i.1) providing a zeolitic starting material having an MWW-type framework structure, wherein the framework structure of the zeolitic starting material comprises $X_2O_3$ and $YO_2$, preferably $B_2O_3$ and $SiO_2$, and the molar ratio $X_2O_3:YO_2$, preferably $B_2O_3$ and $SiO_2$, is at least 0.03:1, preferably in the range of from 0.03:1 to 0.09:1, more preferably 0.03:1 to 0.08:1, more preferably from 0.03:1 to 0.07:1;

(i.2) creating vacant tetrahedral framework sites by treating the zeolitic starting material provided in (i.1) with a liquid solvent system, preferably under reflux, obtaining a zeolitic material having a molar ratio $X_2O_3:YO_2$, preferably $B_2O_3$ and $SiO_2$, of less than 0.03:1, wherein the liquid solvent system is preferably selected from the group consisting of water, methanol, ethanol, propanol, ethane-1,2-diol, propane-1,2-diol, propane-1,3-diol, propane-1,2,3-triol, and mixtures of two or more thereof, the liquid solvent system more preferably being water, wherein more preferably, the liquid solvent system does not contain an inorganic or organic acid, or a salt thereof, and wherein the treating is preferably carried out at a temperature in the range of from 50 to 125° C., more preferably from 90 to 115° C., more preferably from 95 to 105° C., and preferably for a period in the range of from 6 to 20 h, more preferably from 7 to 17 h, more preferably from 8 to 12 h.

Step (i.1)

Generally, there are no specific restrictions how the zeolitic material having an MWW-type framework structure is provided in (i.1). For example, it may be conceivable to purchase a suitable, commercially available zeolitic material having an MWW-type framework structure. Further, for example, any conceivable process for synthesizing such a zeolite can be employed for providing the zeolitic material. Preferably, the zeolitic material is provided by a process starting from suitable sources of $X_2O_3$ and $YO_2$ in the presence of a suitable template compound, also referred to as structure directing agent.

Preferably, the zeolitic material having an MWW-type framework structure is provided in (i.1) by a process comprising (i.1.1) hydrothermally synthesizing a precursor of a zeolitic material having an MWW-type framework structure from an aqueous synthesis mixture containing a source for Y, preferably a silicon source, more preferably ammonia stabilized colloidal silica, a source for Y, preferably a boron source, preferably boric acid, and an MWW template compound, preferably selected from the group consisting of piperidine, hexamethylene imine. N,N,N,N',N',N'-hexamethyl-1,5-pentanediammonium ion, 1,4-bis(N-methylpyrrolidinium)butane, octyltrimethylammonium hydroxide, heptyltrimethylammonium hydroxide, hexyltrimethylammonium hydroxide, and a mixture of two or more thereof, to obtain the precursor of a zeolitic material having an MWW-type framework structure in its mother liquor;

(i.1.2) separating the precursor of a zeolitic material having an MWW-type framework structure from its mother liquor, preferably comprising drying the precursor of a zeolitic material having an MWW-type framework structure, wherein in the synthesis mixture in (i.1.1), the molar ratio of X, calculated as $X_2O_3$ and contained in the source for X, preferably of B, calculated as $B_2O_3$ and contained in the boron source, relative to Y, calculated as $YO_2$ and contained in the source for Y, preferably of Si, calculated as $SiO_2$ and contained in the Si source, is preferably in the range of from 0.4:1 to 0.6:1, more preferably from 0.45:1 to 0.55:1, more preferably from 0.47:1 to 0.52:1;

the molar ratio of the MWW template compound, relative to Y, calculated as $YO_2$ and contained in the source for Y, preferably relative to Si, calculated as $SiO_2$ and contained in the Si source, is preferably in the range of from 0.8:1 to 1.7:1, more preferably from 1.0:1 to 1.5:1, more preferably from 1.1:1 to 1.3:1; and the molar ratio of $H_2O$ relative to Y, calculated as $YO_2$ and contained in the source for Y, preferably relative to Si, calculated as $SiO_2$ and contained in the Si source, is preferably in the range of from 12:1 to 20:1, more preferably from 13:1 to 18:1, more preferably from 14:1 to 16; 1.

Step (i.1.1)

As far as the silicon source used in (i.1.1) is concerned, no specific restrictions exist. Preferably, the silicon source is a fumed silica or a colloidal silica such as ammonia-stabilized colloidal silica, with ammonia-stabilized colloidal silica being especially preferred.

Concerning preferred sources of titanium, titanium oxide, titanium halide and tetraalkylorthotitanates may be mentioned. Among these, titanium halides and tetraalkylorthotitanates are more preferred. More preferred are titanium tetrafluoride, tetraethylorthotitanate, tetrapropylorthotitanate, and tetrabutylorthotitanate, with tetrabutylorthotitanate being especially preferred. Concerning preferred sources of zirconium, zirconium oxide, zirconium halides and zirconium tetraalkoxides may be mentioned. Among these, zirconium halides and zirconium tetraalkoxides are more preferred. More preferred are zirconium tetrafluoride, zirconium tetraethoxide, and zirconium tetrabutoxide. Concerning preferred Germanium sources, germanium oxide, germanium chloride, and germanium isopropoxide may be mentioned.

As far as the boron source used in (i.1.1) is concerned, no specific restrictions exist.

Preferably, the boron source is boric acid, a borate, in particular a water-soluble borate, a boron halide, boron oxide ($B_2O_3$), with boric acid being especially preferred.

Concerning preferred sources of aluminum, alumina, aluminum nitrate may be mentioned, with aluminum nitrate being especially preferred. Concerning preferred sources of indium, indium oxide, indium halides and trialkoxy indium may be mentioned, with indium trichloride, indium trifluoride, and indium triisoproxide being especially preferred. Concerning preferred sources of gallium, gallium oxide, gallium halides and gallium nitrate may be mentioned, with gallium nitrate, gallium trichloride, and gallium trifluoride being especially preferred. Concerning preferred sources of iron, iron oxide, iron halides, iron acetate and iron nitrate may be mentioned, with iron nitrate being especially preferred.

As far as the amounts of the source for X, preferably the silicon source, and the source for Y, preferably the boron source, in (i.1.1) are concerned, no specific restrictions exist provided that the precursor of a zeolitic material having an MWW-type framework structure is obtained. Preferably, the molar ratio of X, calculated as $X_2O_3$ and contained in the source for X, relative to Y, calculated as $YO_2$ and contained in the source for Y, preferably the molar ratio of B, calculated as $B_2O_3$ and contained in the boron source, relative to Si, calculated as $SiO_2$ and contained in the Si source, is at least 0.4:1, preferably in the range of from 0.4:1 to 1:1, more preferably from from 0.4:1 to 0.8:1, more preferably from 0.4:1 to 0.6:1, preferably from 0.45:1 to 0.55:1, more preferably from 0.47:1 to 0.52:1.

As far as the MWW template compound in (i.1.1) is concerned, no specific restrictions exist provided that the precursor of a zeolitic material having an MWW-type framework structure is obtained. Preferably, the MWW template compound is selected from the group consisting of piperidine, hexamethylene imine, N,N,N,N',N',N'-hexamethyl-1,5-pentanediammonium ion, 1,4-bis(N-methylpyrrolidinium)-butane, octyltrimethylammonium hydroxide, heptyltrimethylammonium hydroxide, hexyl-trimethylammonium hydroxide, and a mixture of two or more thereof. More preferably, the MWW template compound is piperidine.

As far as the amounts of the source for Y, preferably the silicon source, and MWW template compound in (i.1.1) are concerned, no specific restrictions exist provided that the precursor of a zeolitic material having an MWW-type framework structure is obtained. Preferably, in (i.1.1), the molar ratio of the MWW template compound, relative to Y, calculated as $YO_2$ and contained in the source for Y, preferably the molar ratio of the MWW template compound, relative to Si, calculated as $SiO_2$ and contained in the Si source, is in the range of from 0.8:1 to 1.7:1, preferably from 1.0:1 to 1.5:1, more preferably from 1.1:1 to 1.3:1.

As far as the amounts of the source for Y, preferably the silicon source, and water in (i.1.1) are concerned, no specific restrictions exist provided that the precursor of a zeolitic material having an MWW-type framework structure is obtained. Preferably, in (i.1.1), the molar ratio of $H_2O$ relative to Y, calculated as $YO_2$ and contained in the source for Y, and the molar ratio of $H_2O$ relative to Si, calculated as $SiO_2$ and contained in the Si source, is in the range of from 12:1 to 20:1, preferably from 13:1 to 18:1, more preferably from 14:1 to 16:1.

According to (i.1.1), the aqueous synthesis mixture is preferably subjected to a hydrothermal synthesis under autogenous pressure, wherein the zeolitic material is crystallized during the hydrothermal synthesis. For crystallization purposes, it is conceivable to use at least one suitable seeding material such as a zeolitic material having an MWW-type framework structure. Preferably, the crystallization time is in the range of from 3 to 8 days, more preferably from 4 to 6 days. During hydrothermal synthesis, the crystallization mixture may be stirred. The stirring rates as such can be suitably chosen depending, for example, on the volume of the aqueous synthesis mixture, the amount of the starting materials employed, the desired temperature, and the like. For example, the stirring rate is in the range of from 50 to 300 r.p.m. (rounds per minute), such as from 70 to 250 r.p.m. or from 90 to 120 r.p.m.

The temperature applied during the hydrothermal synthesis is preferably in the range of from 160 to 200° C., more preferably from 160° C. to 190° C., more preferably from 160 to 180° C. The amounts of precursor compounds are suitably chosen so that above-described precursor of a zeolitic material having an MWW-type framework structure is obtained having the described preferred compositions.

Step (i.1.2)

After hydrothermal synthesis, the obtained precursor of a zeolitic material having an MWW-type framework structure is preferably suitably separated from its mother liquor according to (i.1.2). All conceivable methods of separating a precursor of a zeolitic material having an MWW-type framework structure from its mother liquor are possible. These methods include, for example, filtration, ultrafiltration, diafiltration and centrifugation methods or, for instance, spray drying processes and spray granulation processes. A combination of two or more of these methods can be applied.

Preferably, the precursor of a zeolitic material having an MWW-type framework structure is separated from its mother liquid by filtration, and the thus obtained material, for example in the form of a filter cake, is preferably subjected to washing with at least one suitable washing agent, preferably to washing with water, at a temperature of up to 50° C., preferably from 15 to 50° C., more preferably from 15 to 35° C., more preferably from 20 to 30° C. If washing is applied, it is preferred to continue the washing process until the washing water has a conductivity of at most 1,000 microSiemens/cm, more preferably of at most 800 microSiemens/cm, more preferably of at most 500 microSiemens/cm.

Optionally, the zeolitic material obtained is subjected to pre-drying, for example by subjecting the zeolitic material to a suitable gas stream such as air, lean air, or technical nitrogen, for a time preferably in the range of from 4 to 10 h, more preferably from 5 to 8 h.

The optionally pre-dried filter cake is preferably dried. Preferably, drying is carried out at a temperature in the range of from 100 to 300° C., more preferably from 150 to 275° C., more preferably from 200 to 250° C. in a suitable atmosphere such as technical nitrogen, air, or lean air. Such drying can be accomplished, for example, in a suitable drying oven, or by spray-drying, wherein for spray-drying, a preferably aqueous suspension is preferably prepared from the optionally pre-dried filter cake. If the drying is accomplished by spray-drying, the drying gas inlet temperature is preferably in the range of from 200 to 250° C., more preferably from 220 to 250° C., and the drying gas outlet temperature is preferably in the range of from 100 to 175° C., more preferably from 120 to 150° C.

If spray-drying is carried out, it is conceivable to subject the mother liquor obtained from (i.1.2) containing the zeolitic material, optionally after concentration, directly to spray-drying. Preferably, the dried filter cake as described above is subjected to spray-drying, optionally after suitable re-suspending of the washed and optionally pre-dried zeolitic material wherein aqueous suspension are preferably prepared having preferred solids content in the range of from 2 to 35 weight-%, preferably from 5 to 25 weight-%, more preferably from 10 to 20 weight-%, based on the total weight of the suspension.

Step (i.1.3)

After the preferred drying, the precursor of a zeolitic material having an MWW-type framework structure is subjected to calcination to obtain the zeolitic material having an MWW-type framework structure. During calcination, the MWW template compound is preferably at least partially, more preferably essentially completely removed from the framework structure. Preferred calcination temperatures are the range of from 400 to 700° C., more preferably from 500 to 675° C., more preferably from 550 to 650° C. Preferred atmosphere under which the calcination is carried out include technical nitrogen, air, or lean air. Preferred calcination times are in the range of from 0.5 to 12 h, more preferably from 1 to 10 h, more preferably from 2 to 6 h.

Therefore, the process of the present invention preferably comprises (i.1.3) calcining the precursor of a zeolitic material having an MWW-type framework structure obtained from (i.1.2), obtaining a zeolitic material having an MWW-type framework structure.

Thus, the present invention also relate relates to the process above, wherein the zeolitic material having an MWW-type framework structure is provided in (i.1) by a process comprising (i.1.1) hydrothermally synthesizing a precursor of a zeolitic material having an MWW-type framework structure from an aqueous synthesis mixture containing a source for Y, preferably a silicon source, more preferably ammonia stabilized colloidal silica, a source for Y, preferably a boron source, preferably boric acid, and an MWW template compound, preferably selected from the group consisting of piperidine, hexamethylene imine. N,N,N,N',N', N'-hexamethyl-1,5-pentanediammonium ion, 1,4-bis(N-methylpyrrolidinium)butane, octyltrimethylammonium hydroxide, heptyltrimethylammonium hydroxide, hexyltrimethylammonium hydroxide, and a mixture of two or more thereof, to obtain the precursor of a zeolitic material having an MWW-type framework structure in its mother liquor;

(i.1.2) separating the precursor of a zeolitic material having an MWW-type framework structure from its mother liquor, comprising drying, preferably comprising spray-drying the precursor of a zeolitic material having an MWW-type framework structure;

(i.1.3) calcining the precursor of a zeolitic material having an MWW-type framework structure obtained from (i.1.2), preferably at a temperature in the range of from 400 to 700° C., more preferably from 500 to 675° C., more preferably from 550 to 650° C., preferably for a period of time in the range of from 0.5 to 12 h, more preferably from 1 to 10 h, more preferably from 2 to 6 h, obtaining a zeolitic material having an MWW-type framework structure;

wherein in the synthesis mixture in (i.1.1), the molar ratio of X, calculated as $X_2O_3$ and contained in the source for X, preferably of B, calculated as $B_2O_3$ and contained in the boron source, relative to Y, calculated as $YO_2$ and contained in the source for Y, preferably of Si, calculated as $SiO_2$ and contained in the Si source, is preferably in the range of from 0.4:1 to 0.6:1, more preferably from 0.45:1 to 0.55:1, more preferably from 0.47:1 to 0.52:1;

the molar ratio of the MWW template compound, relative to Y, calculated as $YO_2$ and contained in the source for Y, preferably relative to Si, calculated as $SiO_2$ and contained in the Si source, is preferably in the range of from 0.8:1 to 1.7:1, more preferably from 1.0:1 to 1.5:1, more preferably from 1.1:1 to 1.3:1; and the molar ratio of $H_2O$ relative to Y, calculated as $YO_2$ and contained in the source for Y, preferably relative to Si, calculated as $SiO_2$ and contained in the Si source, is preferably in the range of from 12:1 to 20:1, more preferably from 13:1 to 18:1, more preferably from 14:1 to 16:1.

Generally, the framework structure of the zeolitic material provided in (i) comprises $X_2O_3$ and $YO_2$, preferably $B_2O_3$ and $SiO_2$. Preferably, the suitable sources for $X_2O_3$ and $YO_2$, preferably for $B_2O_3$ and $SiO_2$, as described above are employed in an amount and subjected to hydrothermal synthesis conditions so that at least 95 weight-%, preferably at least 98 weight-%, more preferably at least 99 weight-%, more preferably at least 99.5 weight-% such as at least 99.6 weight-%, at least 99.7 weight-%, at least 99.8 weight-%, or at least 99.9 of the framework structure of the zeolitic material having an MWW-type framework structure provided in (i.1) consist of $X_2O_3$ and $YO_2$, preferably $B_2O_3$ and $SiO_2$. In particular, the zeolitic material having an MWW-type framework structure provided in (i.1) is free of aluminum which, in the context of the present invention, relates to a B-MWW which may contain aluminum only in traces as impurity.

Generally, the molar ratio $X_2O_3$:$YO_2$, preferably $B_2O_3$:$SiO_2$ of the framework structure of the zeolitic material having an MWW-type framework structure is not specifically restricted. Preferably, molar ratio $X_2O_3$:$YO_2$, preferably $B_2O_3$:$SiO_2$ of the zeolitic material having an MWW-type framework structure is at least 0.03:1, preferably in the range of from 0.03:1 to 0.1:1, more preferably from 0.03:1 to 0.09:1, more preferably from 0.03:1 to 0.08:1, more preferably from 0.03:1 to 0.07:1. Thus conceivable preferred molar ratios $X_2O_3$:$YO_2$, $B_2O_3$:$SiO_2$, are in the range of from 0.03:1 to 0.06:1 or from 0.03:1 to 0.05:1 or from 0.03:1 to 0.04:1 or from 0.04:1 to 0.07:1 or from 0.04:1 to 0.06:1 or from 0.04:1 to 0.05:1 or from 0.05 to 1 to 0.07:1 or from 0.05:1 to 0.06:1 or from 0.06:1 to 0.07:1.

Step (i.2)

According to step (i.2) of the process of the present invention, vacant tetrahedral framework sites are created by treating the zeolitic starting material provided in (i.1) with a liquid solvent system. Preferably, the separated, spray-dried and calcined zeolitic material, provided in (i.1), is subjected to a treatment according to (i.2) with a liquid solvent system wherefrom a zeolitic material having a molar ratio $X_2O_3$:$YO_2$, preferably $B_2O_3$:$SiO_2$, of less than 0.03:1 is obtained.

Generally, no specific restrictions exist concerning the chemical nature of the liquid solvent system used in (i.2). Thus, it is conceivable to use an acidic aqueous system for decreasing the molar ratio $X_2O_3$:$YO_2$, preferably $B_2O_3$:$SiO_2$, of the zeolitic material to a value of less than 0.03:1. As acids, the liquid solvent system may comprise, for example, hydrochloric acid, sulfuric acid, nitric acid, phosphoric acid, formic acid, acetic acid, propionic acid, oxalic acid, or tartaric acid. Preferably, the liquid solvent system used in (i.2) is selected from the group consisting of water, monohydric alcohols, polyhydric alcohols, and mixtures of two or more thereof. Concerning the monohydric alcohols and polyhydric alcohols, no specific restrictions exist. Preferably, these alcohols contain from 1 to 6 carbon atoms, more preferably from 1 to 5 carbon atoms, more preferably from 1 to 4 carbon atoms, and more preferably from 1 to 3 carbon atoms. The polyhydric alcohols preferably comprise from 2 to 5 hydroxyl groups, more preferably from 2 to 4 hydroxyl groups, preferably 2 or 3 hydroxyl groups. Especially preferred monohydric alcohols are methanol, ethanol, and propanol like 1-propanol and 2-propanol. Especially preferred polyhydric alcohols are ethane-1,2-diol, propane-1,2-diol, propane-1,3-diol, propane-1,2,3-triol. If mixtures of two or more of above-described compounds are employed, it is preferred that these mixtures comprise water and at least one monohydric and/or at least one polyhydric alcohol. Most preferably, the liquid solvent system consists of water. Therefore, the present invention relates to above-defined process and zeolitic material obtainable or obtained therefrom, wherein the liquid solvent system is selected from the group consisting of water, methanol, ethanol, propanol, ethane-1,2-diol, propane-1,2-diol, propane-1,3-diol, propane-1,2,3-triol, and mixtures of two or more thereof, preferably water.

Further, it is especially preferred that the liquid solvent system does not contain an inorganic acid or an organic acid or a salt thereof, the acid being selected from the group consisting of hydrochloric acid, sulfuric acid, nitric acid, phosphoric acid, formic acid, acetic acid, propionic acid, oxalic acid, and tartaric acid. Therefore, the present invention also relates to the process above, wherein the liquid solvent system is selected from the group consisting of water, methanol, ethanol, propanol, ethane-1,2-diol, propane-1,2-diol, propane-1,3-diol, propane-1,2,3-triol, and mixtures of two or more thereof, preferably water, and wherein the liquid solvent system does not contain an inorganic or organic acid, or a salt thereof, the acid being selected from the group consisting of hydrochloric acid, sulfuric acid, nitric acid, phosphoric acid, formic acid, acetic acid, propionic acid, oxalic acid, and tartaric acid. Even more preferably, the present invention also relates to the process above, wherein the liquid solvent system is selected from the group consisting of water, methanol, ethanol, propanol, ethane-1,2-diol, propane-1,2-diol, propane-1,3-diol, propane-1,2,3-triol, and mixtures of two or more thereof, preferably water, and wherein the liquid solvent system does not contain an inorganic or organic acid, or a salt thereof.

The reaction conditions according to (i.2) are not specifically restricted, provided that the solvent system described above is in its liquid state and that the molar ratio $X_2O_3$:$YO_2$, preferably $B_2O_3$:$SiO_2$, is decreased to a value of at most 0.02:1. In particular, concerning the preferred temperatures described below, the skilled person will choose the respective pressure under which the treating is carried out in order to keep the solvent system in its liquid state. Concerning the duration of the treating according to (i.2), no specific restrictions exist. The above mentioned time is to be understood as the time where the liquid solvent system is maintained under the below described treating temperature. Preferably, in (i.2), the treating is carried out for a period of from 6 to 20 h, more preferably from 7 to 17 h, more preferably from 8 to 12 h. The preferred treating temperatures are in the range of from 50 to 125° C., preferably from 90 to 115° C., more preferably from 95 to 105° C. Most preferably, the treating according to (i.2) is carried out at the boiling point of the solvent system. If the solvent system is comprised of two or more components, the treating according to (i.2) is preferably carried out at the boiling point of the component having the lowest boiling point.

Preferably, the treating according to (i.2) is carried out under reflux. Thus, the preferred vessel, representing an open system, used for the treating according to (i.2) is preferably equipped with a reflux condenser. During the treating according to (i.2), the temperature of the liquid solvent system is kept essentially constant or changed, the treating with the liquid solvent system thus being carried out at two or more different temperatures. Most preferably, the temperature is kept essentially constant within the above-defined ranges.

Therefore, the present invention relates to the process above, comprising (i.2) treating the zeolitic material provided in (i.1) with a liquid solvent system, preferably water, thereby obtaining a zeolitic material having a molar ratio $X_2O_3$:$YO_2$, preferably $B_2O_3$:$SiO_2$, of less than 0.03:1 in an open system under reflux at a temperature in the range of from 95 to 105° C., and at least partially separating the zeolitic material from the liquid solvent system.

As far as the amount of zeolitic material which is employed relative to the amount of liquid solvent system, no specific restrictions exist. Preferably, the weight ratio of zeolitic material relative to the liquid solvent system is in the range of from 1:5 to 1:50, more preferably from 1:10 to 1:35, more preferably from 1:10 to 1:20, even more preferably from 1:12 to 1:18.

During treating according to (i.2), it is further preferred to suitably stir the liquid solvent system. During (i.2), the stirring rate is kept essentially constant or changed, the treating thus being carried out at two or more different stirring rates. Most preferably, the zeolitic material is suspended in the liquid solvent system at a first stirring rate, and during (i.2) at the above-described temperatures, the stirring rate is changed, preferably increased. The stirring rates as such can be suitably chosen depending, for example, on the volume of the liquid solvent system, the amount of the zeolitic material employed, the desired temperature, and the like. Preferably, the stirring rate under which the zeolitic material is suspended in the liquid solvent system is in the range of from 5 to 200 r.p.m. (rounds per minute), more preferably from 10 to 200 r.p.m., more preferably from 20 to 55 r.p.m., more preferably from 30 to 50 r.p.m. The stirring rate under which the treating at the above-described temperatures is carried out is preferably in the range of from 50 to 100 r.p.m., more preferably from 55 to 90 r.p.m., more preferably from 60 to 80 r.p.m.

After the treating according to (i.2), the obtained zeolitic material is preferably separated from the liquid solvent system. Therefore, the present invention also relates to the process above, further comprising (i.3) at least partially separating the zeolitic material obtained from (i.2) from the liquid solvent system, optionally including drying.

Step (i.3)

All methods of separating the zeolitic material from the liquid solvent system are conceivable. These methods include, for example, filtration, ultrafiltration, diafiltration and centrifugation methods or, for instance, spray-drying processes and spray granulation processes, wherein filtration methods can involve suction and/or pressure filtration steps. A combination of two or more of these methods can be applied.

With respect to one or more optional washing procedures, any conceivable solvent can be used. Washing agents which may be used are, for example, water, alcohols, such as methanol, ethanol or propanol, or mixtures of two or more thereof. Examples of mixtures are mixtures of two or more alcohols, such as methanol and ethanol or methanol and propanol or ethanol and propanol or methanol and ethanol and propanol, or mixtures of water and at least one alcohol, such as water and methanol or water and ethanol or water and propanol or water and methanol and ethanol or water and methanol and propanol or water and ethanol and propanol or water and methanol and ethanol and propanol. Water or a mixture of water and at least one alcohol, preferably water and ethanol, is preferred, distilled water being very particularly preferred as the only washing agent.

If washing as applied, it may be preferred to continue the washing process until the washing water has a conductivity of at most 1,000 microSiemens/cm, more preferably of at most 850 microSiemens/cm, more preferably of at most 700 microSiemens/cm.

According to the present invention, the zeolitic material is preferably separated from the suspension by filtration to obtain a filter cake which is preferably subjected to washing, preferably with water.

After separation of the zeolitic material having an MWW-type framework structure from the liquid solvent system, preferably achieved by filtration, and after washing, the zeolitic material obtained in (ii) is optionally subjected to drying. The drying procedure can optionally comprise one or more drying steps. In general, any conceivable means of drying can be used. Drying procedures preferably include heating and/or applying vacuum to the zeolitic material having an MWW-type framework structure.

Preferably, the separated and washed zeolitic material is subjected to pre-drying, for example by subjecting the filter cake to a suitable gas stream, such as air, lean air, or nitrogen, for a time preferably in the range of from 4 to 10 h, more preferably from 5 to 8 h.

Preferably, after the optional pre-drying, the zeolitic material is subjected to drying. Preferably, drying is carried out at a temperature in the range of from 100 to 300° C., more preferably from 100 to 180° C., more preferably from 110 to 140° C. in a suitable atmosphere such as technical nitrogen, air, or lean air. Preferred drying time periods are in the range of from 1 to 48 h, preferably from 2 to 24 h, more preferably from 6 to 18 h.

Therefore, the present invention also relates to the process above, comprising (i.3) at least partially separating the zeolitic material obtained from (i.2) from the liquid solvent system including drying, preferably being carried out at a temperature in the range of from 100 to 180° C., more preferably from 110 to 140° C.

Drying can also be carried out by spray-drying. If spray-drying is carried out, the drying gas inlet temperature is preferably in the range of from 200 to 250° C., more preferably from 220 to 250° C., and the drying gas outlet temperature is preferably in the range of from 100 to 175° C., more preferably from 120 to 150° C. If spray-drying is carried out, it is conceivable to subject the suspension containing the zeolitic material obtained from (i.2), optionally after concentration, directly to spray-drying. Further, it is conceivable to subject the separated and washed zeolitic material to spray-drying, preferably after suitable re-suspending of the washed and optionally pre-dried zeolitic material, preferably in de-ionized water. Preferably, the solid content of the aqueous suspension is in the range of from 2 to 35 weight-%, preferably from 5 to 25 weight-%, more preferably from 10 to 20 weight-%, based on the total weight of the suspension.

Preferably, the zeolitic material obtained from 0.3) is in the form of a powder, preferably in the form of a spray powder wherein the spray-powder may result either from spray-drying in (i.1) and/or spray-drying in (i.3).

Therefore, according to (i), the zeolitic material having an MWW-type framework structure having vacant tetrahedral framework sites is preferably provided by a method comprising (i.1) providing a zeolitic starting material having an MWW-type framework structure, wherein the framework structure of the zeolitic starting material comprises $X_2O_3$ and $YO_2$ and the molar ratio $X_2O_3$:$YO_2$ is at least 0.03:1, preferably in the range of from 0.03:1 to 0.09:1, more preferably from 0.03:1 to 0.08:1, more preferably from 0.03:1 to 0.07:1;

(i.2) creating vacant tetrahedral framework sites by treating the zeolitic starting material provided in (i.1) with a liquid solvent system, preferably under reflux, obtaining a zeolitic material having a molar ratio $X_2O_3:YO_2$ of less than 0.03:1, wherein the liquid solvent system is preferably selected from the group consisting of water, methanol, ethanol, propanol, ethane-1,2-diol, propane-1,2-diol, propane-1,3-diol, propane-1,2,3-triol, and mixtures of two or more thereof, the liquid solvent system more preferably being water, wherein more preferably, the liquid solvent system does not contain an inorganic or organic acid, or a salt thereof, and wherein the treating is preferably carried out at a temperature in the range of from 50 to 125° C., more preferably from 90 to 115° C., more preferably from 95 to 105° C., and preferably for a period in the range of from 6 to 20 h, more preferably from 7 to 17 h, more preferably from 8 to 12 h;

(i.3) at least partially separating the zeolitic material obtained from (i.2) from the liquid solvent system, including drying, preferably being carried out at a temperature in the range of from 100 to 180° C., more preferably from 110 to 140° C.

According to the present invention, the separated zeolitic material obtained from (i.3) is optionally subjected to calcination in a step (i.4).

Step (i.4)

Preferably, the calcination according to (i.4) is carried out in a suitable atmosphere such as air, lean air, or nitrogen at a temperature in the range of from 400 to 800° C., preferably from 600 to 700° C., for a period in the range of from 1 to 10 h, preferably from 2 to 6 h.

Therefore, according to (i), the zeolitic material having an MWW-type framework structure having vacant tetrahedral framework sites is preferably provided by a method comprising (i.1) providing a zeolitic starting material having an MWW-type framework structure, wherein the framework structure of the zeolitic starting material comprises $X_2O_3$ and $YO_2$ and the molar ratio $X_2O_3:YO_2$ is at least 0.03:1, preferably in the range of from 0.03:1 to 0.09:1, more preferably from 0.03:1 to 0.08:1, more preferably from 0.03:1 to 0.07:1;

(i.2) creating vacant tetrahedral framework sites by treating the zeolitic starting material provided in (i.1) with a liquid solvent system, preferably under reflux, obtaining a zeolitic material having a molar ratio $X_2O_3:YO_2$ of less than 0.03:1, wherein the liquid solvent system is preferably selected from the group consisting of water, methanol, ethanol, propanol, ethane-1,2-diol, propane-1,2-diol, propane-1,3-diol, propane-1,2,3-triol, and mixtures of two or more thereof, the liquid solvent system more preferably being water, wherein more preferably, the liquid solvent system does not contain an inorganic or organic acid, or a salt thereof, and wherein the treating is preferably carried out at a temperature in the range of from 50 to 125° C., more preferably from 90 to 115° C., more preferably from 95 to 105° C., and preferably for a period in the range of from 6 to 20 h, more preferably from 7 to 17 h, more preferably from 8 to 12 h;

(i.3) at least partially separating the zeolitic material obtained from (i.2) from the liquid solvent system, including drying, preferably being carried out at a temperature in the range of from 100 to 180° C., more preferably from 110 to 140° C.;

(i.4) optionally calcining the separated zeolitic material obtained from (i.3), preferably at a temperature in the range of from 400 to 800° C., more preferably from 600 to 700° C., and preferably for a time period in the range of from 1 to 10 h, more preferably from 2 to 6 h.

Preferably, the zeolitic material obtained in (i.3) is not subjected to calcination prior to (iii).

Therefore, according to (i), the zeolitic material having an MWW-type framework structure having vacant tetrahedral framework sites is preferably provided by a method comprising (i.1) providing a zeolitic starting material having an MWW-type framework structure, wherein the framework structure of the zeolitic starting material comprises $X_2O_3$ and $YO_2$ and the molar ratio $X_2O_3:YO_2$ is at least 0.03:1, preferably in the range of from 0.03:1 to 0.09:1, more preferably from 0.03:1 to 0.08:1, more preferably from 0.03:1 to 0.07:1;

(i.2) creating vacant tetrahedral framework sites by treating the zeolitic starting material provided in (i.1) with a liquid solvent system, preferably under reflux, obtaining a zeolitic material having a molar ratio $X_2O_3:YO_2$ of less than 0.03:1, wherein the liquid solvent system is preferably selected from the group consisting of water, methanol, ethanol, propanol, ethane-1,2-diol, propane-1,2-diol, propane-1,3-diol, propane-1,2,3-triol, and mixtures of two or more thereof, the liquid solvent system more preferably being water, wherein more preferably, the liquid solvent system does not contain an inorganic or organic acid, or a salt thereof, and wherein the treating is preferably carried out at a temperature in the range of from 50 to 125° C. more preferably from 90 to 115° C., more preferably from 95 to 105° C., and preferably for a period in the range of from 6 to 20 h, more preferably from 7 to 17 h, more preferably from 8 to 12 h;

(i.3) at least partially separating the zeolitic material obtained from (i.2) from the liquid solvent system, including drying, preferably being carried out at a temperature in the range of from 100 to 180° C., more preferably from 110 to 140° C.;

wherein after (i.3) and before (iii), the preferably dried zeolitic material is not subjected to calcination at a temperature in the range of from 600 to 700° C. and a time period in the range of from 2 to 6 h, preferably not subjected to calcination at a temperature in the range of from 400 to 800° C. and a time period in the range of from 1 to 10 h, more preferably not subjected to calcination.

According to the present invention, the treatment according to (ii) with the liquid solvent system decreases the molar ratio $X_2O_3:YO_2$, preferably $B_2O_3:SiO_2$, of the zeolitic material; thus, it is a procedure for removing at least a portion of X from the MWW-type framework structure and creating vacant tetrahedral sites in the zeolitic framework. Therefore, the molar ratio $X_2O_3:YO_2$, preferably $B_2O_3:SiO_2$, of the zeolitic material having an MWW-type framework structure obtained from (ii) is higher than the molar ratio $X_2O_3:YO_2$, preferably $B_2O_3:SiO_2$, of the zeolitic material having an MWW-type framework structure provided in (i). According to a preferred embodiment of the present invention, the molar ratio $X_2O_3:YO_2$, preferably $B_2O_3:SiO_2$, obtained in (ii) is at most 0.01:1, preferably in the range of from 0.001:1 to 0.01:1, more preferably from 0.001:1 to 0.009:1, more preferably from 0.001:1 to 0.008:1, more preferably from 0.001:1 to 0.007:1, more preferably from 0.001:1 to 0.006:1, more preferably from 0.001:1 to 0.005:1, more preferably from 0.001:1 to 0.004:1, more preferably from 0.001:1 to 0.003:1.

Therefore, the present invention relates to the process above, wherein in the framework structure of the zeolitic material provided in (i), the molar ratio $X_2O_3:YO_2$, preferably $B_2O_3:SiO_2$, is at most 0.01:1, preferably in the range of from 0.001:1 to 0.01:1, more preferably from 0.001:1 to 0.009:1, more preferably from 0.001:1 to 0.008:1, more preferably from 0.001:1 to 0.007:1, more preferably from 0.001:1 to 0.006:1, more preferably from 0.001:1 to 0.005:1, more preferably from 0.001:1 to 0.004:1, more preferably from 0.001:1 to 0.003:1.

Therefore, the present invention also relates to the process above, wherein n the framework structure of the zeolitic material provided in (i), the molar ratio $X_2O_3:YO_2$ is at most 0.01:1, preferably in the range of from 0.001:1 to 0.01:1, more preferably from 0.001:1 to 0.003:1.

According to the present invention, it is preferred to provide a zeolitic material having an MWW-type framework structure based on a $SiO_2$ source and a $B_2O_3$ source. It is especially preferred that the zeolitic material having an MWW-type framework structure is free of aluminum. The term "free of aluminum" as used in this context of the present invention relates to a zeolitic material having an MWW-type framework structure which may contain aluminum only in traces as impurities which may result, for example, from aluminum impurities in the starting materials present in the synthesis mixture used for the preparation of the zeolitic material, that is as impurities in the silicon source, the boron source, the template compound, and the water. In particular, no aluminum source is used in the synthesis mixture in (i.1).

Preferably, at least 95 weight-%, preferably at least 98 weight-%, more preferably at least 99 weight-% of the framework structure of the zeolitic material provided in (i) consist of $X_2O_3$ and $YO_2$, preferably $B_2O_3$ and $SiO_2$. More preferably, at least 99.5 weight-%, more preferably at least 99.8 weight-%, more preferably at least 99.9 weight-% of the framework structure of the zeolitic material provided in (i) consist of $X_2O_3$ and $YO_2$, preferably $B_2O_3$ and $SiO_2$.

Therefore, the present invention also relates to the process above, wherein at least 95 weight-%, preferably at least 98 weight-%, more preferably at least 99 weight-% of the framework structure of the zeolitic material provided in (i) consist of $X_2O_3$ and $YO_2$.

Based on the composition of the zeolitic material having an MWW-type framework structure which is subjected to the removal of X, preferably B, from the zeolitic framework, and further based on the composition of the zeolitic material having an MWW-type framework structure obtained from the removal of X, preferably B, from the zeolitic framework, the molar amount of the vacant tetrahedral framework sites formed by the removal stage can be easily calculated.

Step (ii)

According to step (ii) of the process of the present invention, a tin-ion source is provided in solid form.

Generally, there are no specific restrictions regarding the tin-ion source, provided that tin can be incorporated in the zeolitic framework according to (iii) by solid-state ion exchange.

Preferably, the tin-ion source is selected from the group consisting of tin(II) alkoxides, tin(IV) alkoxides, tin(II) salts of organic acids, tin(IV) salts of organic acids, and a mixture a two or more thereof. More preferably, the tin-ion source is selected from the group consisting of tin(II) alkoxides having from 1 to 4 carbon atoms such as 1 carbon atom, 2 carbon atoms, 3 carbon atoms, or 4 carbon atoms, tin(IV) alkoxides having from 1 to 4 carbon atoms such as 1 carbon atom, 2 carbon atoms, 3 carbon atoms, or 4 carbon atoms, tin(II) salts of organic acids having from 1 to 6 carbon atoms such as 1 carbon atom, 2 carbon atoms, 3 carbon atoms, 4 carbon atoms, 5 carbon atoms, or 6 carbon atoms, tin(IV) salts of organic acids having from 1 to 6 carbon atoms such as 1 carbon atom, 2 carbon atoms, 3 carbon atoms, 4 carbon atoms, 5 carbon atoms, or 6 carbon atoms, and a mixture a two or more thereof. More preferably, the tin-ion source includes a tin(II) salt of organic acids having from 1 to 6 carbon atoms such as 1 carbon atom, 2 carbon atoms, 3 carbon atoms, 4 carbon atoms, 5 carbon atoms, or 6 carbon atoms, or a tin(IV) salt of organic acids having from 1 to 6 carbon atoms such as 1 carbon atom, 2 carbon atoms, 3 carbon atoms, 4 carbon atoms, 5 carbon atoms, or 6 carbon atoms. More preferably, the tin-ion source includes a tin(II) salt of organic acids having from 1 to 6 carbon atoms such as 1 carbon atom, 2 carbon atoms, 3 carbon atoms, 4 carbon atoms, 5 carbon atoms, or 6 carbon atoms. More preferably, the tin-ion source includes tin(II) acetate.

Therefore, the present invention relates to the process above, wherein the tin-ion source provided in (ii) is selected from the group consisting of tin(II) alkoxides, tin(IV) alkoxides, tin(II) salts of organic acids, tin(IV) salts of organic acids, and a mixture a two or more thereof, preferably from the group consisting of tin(II) alkoxides having from 1 to 4 carbon atoms, tin(IV) alkoxides having from 1 to 4 carbon atoms, tin(II) salts of organic acids having from 1 to 6 carbon atoms, tin(IV) salts of organic acids having from 1 to 6 carbon atoms, and a mixture a two or more thereof, wherein more preferably, the tin-ion source provided in (ii) is tin(II) acetate.

Step (iii)

According to step (iii) of the process of the present invention, tin is incorporated into the zeolitic material provided in (i) by bringing the zeolitic material provided in (i) in contact with the tin-ion source provided in (ii) under solid-state ion exchange conditions, obtaining a tin-containing zeolitic material having an MWW-type framework structure.

Regarding the amount of the tin-ion source and the amount of the zeolitic material employed in (iii), no specific restrictions exist. Generally, the amount of the tin-ion source will be chosen depending on the desired tin content of the tin-containing zeolitic material which is prepared. Preferably according to the present invention, tin-containing zeolitic material having a high tin content are prepared. Therefore, it is preferred that the tin-ion source is employed in an amount relative to the amount of the zeolitic material having vacant tetrahedral framework sites so that up to 100% of the vacant tetrahedral sites can be filled with tin. Since the molar amount of the vacant tetrahedral framework sites formed by the removal stage can be easily calculated as described above, the necessary amount of the tin-ion source in turn can be easily determined. Preferably, according to (iii), the molar ratio of tin contained in the tin-ion source brought into contact with zeolitic material relative to the vacant tetrahedral framework sites of the zeolitic material is at most 1:1.

Therefore, the present invention relates to the process above, wherein according to (iii), the molar ratio of tin contained in the tin-ion source brought into contact with zeolitic material relative to the vacant tetrahedral framework sites of the zeolitic material is at most 1:1.

Depending on the amount vacant tetrahedral framework sites, preferred tin containing materials are prepared according to the present invention having a tin content in the range of from 1 to 20 weight-%, preferably from 2 to 18 weight-%, more preferably from 5 to 16 weight-%, based on the total weight of the tin-containing zeolitic material.

Preferably, tin containing materials are prepared according to the present invention having a tin content of at least 10 weight-%, based on the total weight of the tin-containing zeolitic material. More preferably, tin containing materials are prepared according to the present invention having a tin content in the range of from 10 to 20 weight-%, more preferably from 10.5 to 19 weight-%, more preferably from 11 to 18 weight-%, more preferably from 11.5 to 17 weight-%, more preferably from 12 to 16 weight-%, based on the total weight of the tin-containing zeolitic material.

Regarding the method how the zeolitic material provided in (i) is brought in contact with the tin-ion source provided in (ii) under solid-state ion exchange conditions according to (iii) is not subject to any specific restrictions. Preferably, in (iii), bringing the zeolitic material provided in (i) in contact with the tin-ion source provided in (ii) under solid-state ion exchange conditions comprises mixing the zeolitic material provided in (i) with the tin-ion source.

Any suitable mixing method can be applied. For example, the mixing can be carried out manually or using a suitable mixing apparatus. Manual mixing can be carried, for example, by grinding the zeolitic material provided in (i) together with the tin-ion source provided in (ii), for example in a suitable mortar. Suitable mixing apparatuses include, for example, high energy mixers, grinding mills such as ball mills, rod mills, autogenous mills, semi-autogenous mills, pebble mills, high pressure grinding rolls, buhrstone mills, vertical shaft impactor mills, or tower mills.

Preferably, the mixing is carried out in a suitable apparatus which provides, during mixing, a high energy input, preferably in the range of from 100 to 1,000 W, more preferably from 200 to 800 W, more preferably from 300 to 600 W. If the mixing is carried out in a mixing apparatus which provides the mixing energy by stirring the mixture, it is preferred to carry out the mixing under stirring at a stirring energy input in the range of from 100 to 1000 W, preferably from 200 to 800 W, more preferably from 300 to 600 W.

Preferably, in (iii), the zeolitic material is mixed with the tin-ion source for a time period in the range of from 2 min to 5 h, preferably from 5 min to 3 h, more preferably from 10 min to 2 h.

Therefore, the present invention also relates to the process above, wherein in (iii), tin is incorporated into the zeolitic material provided in (i) by bringing the zeolitic material provided in (i) in contact with the tin-ion source provided in (ii) under solid-state ion exchange conditions, obtaining a tin-containing zeolitic material having an MWW-type framework structure, said solid-state ion exchange conditions comprising mixing the zeolitic material provided in (i) together with the tin-ion source provided in (ii) at an energy input, preferably provided by stirring the mixture of the zeolitic material provided in (i) and the tin-ion source provided in (ii), in in the range of from 100 to 1000 W, preferably from 200 to 800 W, more preferably from 300 to 600 W.

Therefore, the present invention also relates to the process above, wherein in (iii), tin is incorporated into the zeolitic material provided in (i) by bringing the zeolitic material provided in (i) in contact with the tin-ion source provided in (ii) under solid-state ion exchange conditions, obtaining a tin-containing zeolitic material having an MWW-type framework structure, said solid-state ion exchange conditions comprising mixing the zeolitic material provided in (i) together with the tin-ion source provided in (ii) for a time period in the range of from 2 min to 5 h, preferably from 5 min to 3 h, more preferably from 10 min to 2 h, at an energy input, preferably provided by stirring the mixture of the zeolitic material provided in (i) and the tin-ion source provided in (ii), in in the range of from 100 to 1000 W, preferably from 200 to 800 W, more preferably from 300 to 600 W.

According to the process of the present invention, it is possible that prior to mixing the zeolitic material provided in (i) together with the tin-ion source provided in (ii), either the zeolitic material and/or the tin-ion source is grinded or milled separately. Therefore, the present invention also relates to the process above, comprising grinding and/or milling the zeolitic material prior to milling the zeolitic material together with the tin-ion source, or grinding and/or milling the tin-ion source prior to milling the zeolitic material together with the tin-ion source, or grinding and/or milling the zeolitic material prior to milling the zeolitic material together with the tin-ion source and grinding and/or milling the tin-ion source prior to milling the zeolitic material together with the tin-ion source.

Preferably, the process of the present invention further comprises an additional step according to which the zeolitic material obtained from the solid-state ion exchange step described above is subjected to a heat-treatment. Therefore, the present invention also relates to the process above, further comprising (iv) subjecting the zeolitic material obtained from (iii) to a heat-treatment.

Step (iv)

According to step (iv) of the process of the present invention, the zeolitic material obtained from (iii) is subjected to a heat-treatment.

Optionally, said heat treatment comprises drying the zeolitic material obtained from (iii). Such drying can be carried out preferably at a temperature in the range of from 75 to 175° C., more preferably from 100 to 150° C. Said drying can be carried out preferably for a time period in the range of from 2 to 48 h, more preferably from 6 to 24 h. Further, said drying can be carried out under an atmosphere comprising oxygen, such as pure oxygen, air, or lean air, or under an inert atmosphere such as argon or nitrogen, preferably technical nitrogen. Preferably, said drying is carried out at least partially in an atmosphere comprising oxygen.

According to the present invention, it is conceivable that according to step (iv) of the process of the present invention, the zeolitic material obtained from (iii) is subjected to a heat-treatment, which heat-treatment consists of said drying. Therefore, the present invention relates to the process above, wherein according to (iv), the zeolitic material obtained from (iii) is subjected to heat treatment by drying the zeolitic material obtained from (iii), preferably at a temperature in the range of from 75 to 175° C., more preferably from 100 to 150° C., preferably for a time period in the range of from 2 to 48 h, more preferably from 6 to 24 h, preferably at least partially under an atmosphere comprising oxygen, such as pure oxygen, air, or lean air, or under an inert atmosphere such as argon or nitrogen, preferably technical nitrogen, more preferably under an atmosphere comprising oxygen, such as pure oxygen, air, or lean air.

The drying can be carried out in any suitable apparatus, such as a static oven or in a continuous drying apparatus. The drying can include spray-drying the zeolitic material obtained from (iii), preferably after preparing a preferably aqueous suspension containing the zeolitic material obtained from (iii). Preferably, the solid content of the aqueous suspension is in the range of from 2 to 35 weight-%, preferably from 5 to 25 weight-%, more preferably from 10 to 20 weight-%, based on the total weight of the suspension.

Preferably, according to step (iv) of the process of the present invention, the zeolitic material obtained from (iii) is subjected to a heat-treatment, which heat-treatment comprises calcining the zeolitic material. According to one embodiment of the present invention, the heat treatment according to (iv) consists of calcining the zeolitic material. According to another embodiment of the present invention, the heat treatment according to (iv) comprises drying the zeolitic material obtained from (iii), followed by calcining the dried zeolitic material, wherein it is preferred the that heat treatment according to (iv) consists of drying the zeolitic material obtained from (iii), followed by calcining the dried zeolitic material.

According to the present invention, it is conceivable to carry out the calcining in 1, 2, or more subsequent calcination stages wherein in each stage, the calcination conditions can be the same or different from each other. Preferably, the calcination is carried out in at least one stage in an atmosphere comprising oxygen, such as pure oxygen, air, or lean air. Therefore, it is preferred that the calcining according to (iv) is carried out at least partially in an atmosphere comprising oxygen.

Thus, the heat-treating according to (iv) preferably comprises calcining, wherein the calcining is preferably carried out at a temperature in the range of from 400 to 700° C., more preferably from 450 to 600° C., preferably for a time period in the range of from 1 to 10 h, more preferably from 2 to 8 h, preferably at least partially in an atmosphere comprising oxygen, wherein the calcining according to (iv) can be partially carried out in an inert gas atmosphere.

According to a preferred calcination embodiment of the present invention, the calcining according to (iv) is carried out in at least 1 calcination stage wherein in each calcination stage, the calcining is carried out in an atmosphere comprising oxygen. In each of the calcination stages, the calcination temperature is preferably in the range of from 400 to 700° C., more preferably from 450 to 600° C., wherein the calcination temperatures in different stages can be different. The overall calcination time of the at least 1 calcination stage is preferably in the range of from 1 to 10 h, more preferably from 2 to 8 h. Preferably, the zeolitic material obtained from (iii) is heated to the calcination temperature at a heating ramp in the range of from 0.2 to 5 K/min, more preferably from 0.5 to 4 IC/min, more preferably from 1 to 3 K/min. Preferably, if the calcining according to (iv) is completely carried out in an atmosphere comprising oxygen, it is preferred to carry out the calcining in 1 calcination stage.

Therefore, the present invention relates to the process above wherein according to (iv), the zeolitic material obtained from (iii) is subjected to a heat-treatment, which heat-treatment comprises calcining the zeolitic material in 1 calcination stage, at a calcination temperature preferably in the range of from 400 to 700° C., more preferably from 450 to 600° C., for a calcination time preferably in the range of from 1 to 10 h, more preferably from 2 to 8 h, wherein this heat treatment preferably comprises heating the zeolitic material obtained from (iii) to the calcination temperature at a heating ramp in the range of from 0.2 to 5 K/min, more preferably from 0.5 to 4 K/min, more preferably from 1 to 3 K/min.

According to another preferred calcination embodiment of the present invention, the calcining according to (iv) is carried out in at least 2 calcination stages wherein in at least one calcination stage, the calcining is carried out in an atmosphere comprising oxygen, and wherein in at least one calcination stage, the calcining is carried out in an inert atmosphere. In each of the calcination stages, the calcination temperature is preferably in the range of from 400 to 700° C., more preferably from 450 to 600° C., wherein the calcination temperatures in different stages can be different. The overall calcination time of the at least 2 calcination stage is preferably in the range of from 1 to 10 h, more preferably from 2 to 8 h, Preferably, the zeolitic material obtained from (iii) is heated to the calcination temperature at a heating ramp in the range of from 0.2 to 5 K/min, more preferably from 0.5 to 4 K/min, more preferably from 1 to 3 K/min. Preferably, if the calcining according to (iv) is carried out in an atmosphere comprising oxygen and in an inert atmosphere, it is preferred to carry out the calcining in 2 calcination stage wherein in the first calcination stage, the calcining is carried out in an atmosphere comprising oxygen and in the second calcination stage, the calcining is carried out in an inert atmosphere, or wherein in the first calcination stage, the calcining is carried out in an inert atmosphere and in the second calcination stage, the calcining is carried out in an atmosphere comprising oxygen.

Therefore, the present invention relates to the process above wherein according to (iv), the zeolitic material obtained from (iii) is subjected to a heat-treatment, which heat-treatment comprises calcining the zeolitic material in 2 calcination stage, at a calcination temperature in each stage preferably in the range of from 400 to 700° C., more preferably from 450 to 600° C., for a total calcination time preferably in the range of from 1 to 10 h, more preferably from 2 to 8 h, wherein this heat treatment preferably comprises heating the zeolitic material obtained from (iii) to the calcination temperature at a heating ramp in the range of from 0.2 to 5 K/min, more preferably from 0.5 to 4 K/min, more preferably from 1 to 3 K/min, and wherein in the first calcination stage, the calcining is carried out in an inert atmosphere, preferably nitrogen, and in the second calcination stage, the calcining is carried out in an atmosphere comprising oxygen, preferably air or lean air.

Therefore, the present invention relates to the process above wherein according to (iv), the zeolitic material obtained from (iii) is subjected to a heat-treatment, which heat-treatment comprises calcining the zeolitic material in 2 calcination stage, at a calcination temperature in each stage preferably in the range of from 400 to 700° C., more preferably from 450 to 600° C., for a total calcination time preferably in the range of from 1 to 10 h, more preferably from 2 to 8 h, wherein this heat treatment preferably comprises heating the zeolitic material obtained from (iii) to the calcination temperature at a heating ramp in the range of from 0.2 to 5 K/min, more preferably from 0.5 to 4 K/min, more preferably from 1 to 3 K/min, and wherein in the first calcination stage, the calcining is carried out in an atmosphere comprising oxygen, preferably air or lean air, and in the second calcination stage, the calcining is carried out in an inert atmosphere, preferably nitrogen.

The calcining can be carried out in any suitable apparatus, such as a static oven or in a continuous calcining apparatus.

Preferably, the process of the present invention further comprises an additional step according to which the zeolitic material obtained from the solid-state ion exchange step or the heat-treatment step described above is subjected to a treatment with an acidic aqueous solution. Therefore, the present invention also relates to the process above, further comprising (v) treating the zeolitic material obtained from (iii) or (iv), preferably from (iv), with an aqueous solution having a pH of at most 5.

Step (v)

According to step (v) of the process of the present invention, the heat-treated zeolitic material obtained from (iv) is treated with an aqueous solution having a pH of at most 5.

Preferably, the aqueous solution having a pH of at most 5 comprises at least one organic acid, or at least one inorganic acid, or at least one organic acid and at least one inorganic acid. The organic acid is preferably selected from the group consisting of oxalic acid, acetic acid, citric acid, methane sulfonic acid, and a mixture of two or more thereof. The inorganic acid is preferably selected from the group consisting of phosphoric acid, sulphuric acid, hydrochloric acid, nitric acid, and a mixture of two or more thereof. Therefore, the present invention relates to the process above, wherein in (v), the aqueous solution comprises an organic acid, preferably selected from the group consisting of oxalic acid, acetic acid, citric acid, methane sulfonic acid, and a mixture of two or more thereof, and/or comprises an inorganic acid, preferably selected from the group consisting of phosphoric acid, sulphuric acid, hydrochloric acid, nitric acid, and a mixture of two or more thereof. More preferably, the aqueous solution comprises an inorganic acid, preferably selected from the group consisting of phosphoric acid, sulphuric acid, hydrochloric acid, nitric acid, and a mixture of two or more thereof. More preferably, the aqueous solution comprises an inorganic acid, preferably selected from the group consisting of phosphoric acid, sulphuric acid, hydrochloric acid, nitric acid, and a mixture of two or more thereof, and does not comprise an organic acid selected from the group consisting of oxalic acid, acetic acid, citric acid, methane sulfonic acid, and a mixture of two or more thereof, more preferably does not contain an organic acid. More preferably, the aqueous solution comprises nitric acid. More preferably, the aqueous solution comprises nitric acid and does not comprise an organic acid selected from the group consisting of oxalic acid, acetic acid, citric acid, methane sulfonic acid, and a mixture of two or more thereof, more preferably does not contain an organic acid. More preferably, the aqueous solution comprises only nitric acid as acidic compound.

Therefore, the present invention also relates to the process above, wherein in (v), the aqueous solution comprises an organic acid, preferably selected from the group consisting of oxalic acid, acetic acid, citric acid, methane sulfonic acid, and a mixture of two or more thereof, and/or comprises an inorganic acid, preferably selected from the group consisting of phosphoric acid, sulphuric acid, hydrochloric acid, nitric acid, and a mixture of two or more thereof, the inorganic acid more preferably being nitric acid.

Preferably, in (v), the aqueous solution has a pH in the range of from 0 to 5, preferably from 0 to 4.5, more preferably from 0 to 4, more preferably from 0 to 3.5, more preferably from 0 to 3, more preferably from 0 to 2.5, more preferably from 0 to 2.

Concerning the temperature of the treating with the aqueous solution according to (v), no specific restrictions exist. Preferably, in (v), the heat-treated zeolitic material is treated with the aqueous solution at a temperature in the range of from 70° C. to 100° C., preferably from 80° C. to 100° C., more preferably from 90 to 100° C. While concerning the type of vessel in which the treating in (v) is conducted, no particular restrictions exist, the vessel is suitably chosen to allow to treat zeolitic material at the temperatures described above, at which temperatures the aqueous solution is in its liquid state. Therefore, as far as higher temperatures are concerned, the treating in (v) is carried out in a closed system under autogenous pressure.

Concerning the time period of the treating with the aqueous solution according to (v), no specific restrictions exist. Preferably, in (v), the heat-treated zeolitic material is treated with the aqueous solution for a time period in the range of from 10 min to 40 h, preferably from 30 min to 30 h, more preferably from 1 h to 25 h.

As far as the amount of the aqueous solution used in (v) is concerned, no specific restrictions exist. Preferably, the weight ratio of the aqueous solution relative to the heat-treated zeolitic material is in the range of from 2:1 to 50:1, preferably from 8:1 to 40:1, more preferably from 10:1 to 35:1.

Therefore, the present invention relates to the process above, wherein in (v), the heat-treated zeolitic material obtained from (iv) is treated with an aqueous solution having a pH in the range of from 0 to 5, preferably from 0 to 3.5, more preferably from 0 to 2, at a temperature in the range of from 70° C. to 100° C., preferably from 80° C. to 100° C., more preferably from 90 to 100° C., and for a time period in the range of from 10 min to 40 h, preferably from 30 min to 30 h, more preferably from 1 h to 25 h, wherein the weight ratio of the aqueous solution relative to the heat-treated zeolitic material is in the range of from 2:1 to 50:1, preferably from 8:1 to 40:1, more preferably from 10:1 to 35:1.

During the treating according to (v), it is preferred to suitably stir the aqueous solution containing the zeolitic material. During (v), the stirring rate is kept essentially constant or changed. The stirring rate as such can be suitably chosen depending, for example, on the volume of the aqueous solution, the amount of the zeolitic material employed, the desired temperature, and the like. Preferably, the stirring rate under which the treating at the above-described temperatures is carried out is preferably in the range of from 50 to 300 r.p.m. (rounds per minute), more preferably from 100 to 250 r.p.m., more preferably from 180 to 220 r.p.m.

After treating zeolitic material obtained from (iv) with an aqueous solution having a pH of at most 5 according to (v), it is preferred to separate the tin-containing zeolitic material having an MWW-type framework structure from the aqueous solution. All conceivable methods of separating the zeolitic material from the aqueous solution are generally possible. These methods include, for example, filtration, ultrafiltration, diafiltration and centrifugation methods or, for instance, spray drying processes and spray granulation processes. A combination of two or more of these methods can be applied. According to a conceivable embodiment of the present invention, the zeolitic material is separated from the aqueous solution by direct spray-drying. Prior to spray-drying, it is possible to increase the zeolitic material content in the aqueous solution by concentrating the suspension or to decrease the zeolitic material content in the aqueous solution by diluting the suspension. Preferably, the zeolitic material is separated from the aqueous solution by a suitable filtration, and the thus obtained material, for example in the form of a filter cake which is optionally subjected to washing.

Either the spray-dried material, is preferably subjected to washing with at least one suitable washing agent. Washing agents which may be used are, for example, water, alcohols, such as methanol, ethanol or propanol, or mixtures of two or more thereof. Examples of mixtures are mixtures of two or more alcohols, such as methanol and ethanol or methanol and propanol or ethanol and propanol or methanol and ethanol and propanol, or mixtures of water and at least one alcohol, such as water and methanol or water and ethanol or water and propanol or water and methanol and ethanol or water and methanol and propanol or water and ethanol and propanol or water and methanol and ethanol and propanol. Water or a mixture of water and at least one alcohol, preferably water and ethanol, is preferred, distilled water being very particularly preferred as the only washing agent. Preferably, the washing is carried out at a temperature of up to 50° C., more preferably in the range of from 15 to 50° C., more preferably from 15 to 35° C., more preferably from 20 to 30° C. Preferably, the washing is carried out until the pH of the water obtained from the washing has a pH in the range of from 6.5 to 7.5, preferably from 6.7 to 7.3, more preferably from 6.9 to 7.1.

Preferably, the optionally washed zeolitic material is subjected to a step (vi) according to which it is dried and/or calcined. More preferably, the optionally washed zeolitic material is subjected to a step (vi) according to which it is dried and calcined.

Step (vi)

Regarding the drying conditions, no specific restrictions exist. Preferably, the drying is carried out at a temperature in the range of from 90 to 180° C., more preferably from 100 to 150° C. Preferably, the drying is carried out for a time period in the range of from 1 to 24 h, more preferably from 6 to 12 h. The drying can be carried out in an atmosphere comprising oxygen such as pure oxygen, air, or lean air, or in an inert atmosphere such as nitrogen or argon, preferably in an atmosphere comprising oxygen, more preferably in air or lean air. The drying can be carried out in a static oven or in a continuous drying apparatus.

Regarding the calcining conditions, no specific restrictions exist. Preferably, the calcining is carried out at a temperature in the range of from 400 to 700° C., more preferably from 450 to 600° C. Preferably, the calcining is carried out for a time period in the range of from 1 to 24 h, more preferably from 6 to 12 h. The calcining can be carried out in an atmosphere comprising oxygen such as pure oxygen, air, or lean air, or in an inert atmosphere such as nitrogen or argon, preferably in an atmosphere comprising oxygen, more preferably in air or lean air. The calcining can be carried out in a static oven or in a continuous drying apparatus.

Therefore, the present invention relates to the process above, further comprising (vi) drying and/or calcining the zeolitic material obtained from (v), optionally after washing, wherein the drying is preferably carried out at a temperature in the range of from 90 to 180° C., preferably from 100 to 150° C., for a period in the range of from 1 to 24 h, preferably from 6 to 12 h, and calcination is preferably carried out at a temperature in the range of from 400 to 700° C., preferably from 450 to 600° C., for a period in the range of from 1 to 24 h, preferably from 6 to 12 h.

The Tin-Containing Zeolitic Material as Such

According to the present invention, tin-containing zeolites having an MWW-type framework structure are prepared which, compared to tin-containing zeolites having an MWW-type framework structure known in the art may have a higher tin content and exhibit advantageous characteristics if used as catalytically active materials, preferably in oxidation reactions or isomerization reactions, in particular for the isomerization from alpha-pinene oxide to campholenic aldehyde.

Therefore, the present invention also relates to a tin-containing zeolitic material having an MWW-type framework structure, obtainable or obtained by a process as described above, preferably by a process comprising steps (i) to (iii), more preferably by a process comprising steps (i) to (iv), more preferably by a process comprising steps (i) to (v), more preferably by a process comprising steps (i) to (v).

In particular, the present invention relates to a tin-containing zeolitic material having an MWW-type framework structure comprising $X_2O_3$ and $YO_2$, wherein Y is a tetravalent element selected from the group consisting of Si, Ti, Zr, Ge, and combinations of two or more thereof, Y preferably being Si, X is a trivalent element selected from the group consisting of Al, B, In, Ga, Fe, and combinations of two or more thereof, X preferably being B, wherein the framework structure additionally comprises tin, wherein in the framework structure of the zeolitic material, the molar ratio $X_2O_3:YO_2$, preferably $B_2O_3:SiO_2$, is at most 0.01:1, preferably in the range of from 0.001:1 to 0.01:1, more preferably from 0.001:1 to 0.003:1, wherein at least 95 weight-%, preferably at least 98 weight-%, more preferably at least 99 weight-% of the framework structure of the zeolitic material consist of X, Y, O, and tin, preferably of of B, Si, O, and tin, and wherein the tin-containing zeolitic material has a tin content of at least 10 weight-%, based on the total weight of the tin-containing zeolitic material.

The present invention also relates to the tin-containing zeolitic material having an MWW-type framework structure described above, having a tin content in the range of from 10 to 20 weight-%, more preferably from 10.5 to 19 weight-%, more preferably from 11 to 18 weight-%, more preferably from 11.5 to 17 weight-%, more preferably from 12 to 16 weight-%, based on the total weight of the tin-containing zeolitic material.

Also, the present invention relates to said tin-containing zeolitic material of the present invention, obtainable or obtained by a process as described above, preferably by a process comprising steps (i) to (iii), more preferably steps (i) to (iv), more preferably steps (i) to (v), more preferably steps (i) to (vi).

Further, the present invention relates to the use of the tin-containing zeolitic material having an MWW-type framework structure as described above as a catalytically active material in oxidation reactions, preferably in BaeyerVilliger-type oxidation reactions, more preferably for the BaeyerVilliger oxidation of cyclic ketones, or as a catalytically active material in isomerization reactions, preferably in the isomerization of alpha-pinene oxide to campholenic aldehyde.

Yet further, the present invention relates to an oxidation reaction, preferably a BaeyerVilliger-type oxidation reaction, more preferably the BaeyerVilliger oxidation of a cyclic ketone, or an isomerization reaction, preferably the isomerization of alpha-pinene oxide to campholenic aldehyde, wherein the tin-containing zeolitic material having an MWW-type framework structure as described above is employed as a catalytically active material.

Further Process Steps

Generally, it is possible to employ the zeolitic material according to the present invention, present as a zeolitic powder or a zeolitic spray powder, as such, without any further modifications, for example as a catalyst, as a catalyst support, as a molecular sieve, as an adsorbent, as a filler, or the like.

It is also conceivable that based on the zeolitic material of the present invention, a molding is prepared containing the zeolitic material. In such a process, the zeolitic material, optionally after further modification, is suitably shaped and optionally post-treated. Therefore, the present invention also relates to a process as described above, further comprising (vii) shaping the tin-containing zeolitic material having an MWW-type framework structure obtained from (iii) or (iv) or (v) or (vi), preferably from (iii) or (vi), obtaining a molding.

For the shaping in (vii), the zeolitic material can be admixed with at least one binder and/or with at least one binder precursor, and optionally with at least one pore-forming agent and/or at least one plasticizing agent.

Examples of such binders are metal oxides, such as, for example, $SiO_2$, $Al_2O_3$, $TiO_2$, $ZrO_2$ or MgO or clays or mixtures of two or more of these oxides or mixed oxides of at least two of Si, Al, Ti, Zr, and Mg. Clay minerals and naturally occurring or synthetically produced alumina, such as, for example, alpha-, beta-, gamma-, delta-, eta-, kappa-, chi- or theta-alumina and their inorganic or organometallic precursor compounds, such as, for example, gibbsite, bayerite, boehmite or pseudoboehmite or trialkoxyaluminates, such as, for example, aluminum triisopropylate, are particularly preferred as $Al_2O_3$ binders. Further conceivable binders might be amphiphilic compounds having a polar and a non-polar moiety and graphite. Further binders might be, for example, clays, such as, for example, montmorillonites, kaolins, metakaoline, hectorite, bentonites, halloysites, dickites, nacrites or anaxites. These binders can be used as such or in the form of suitable precursor compounds which, either during spray-drying and/or the subsequent calcination form the desired binder. Examples of such binder precursors are tetraalkoxysilanes, tetraalkoxytitanates, tetraalkoxyzirconates or a mixture of two or more different tetraalkoxysilanes or a mixture of two or more different tetraalkoxytitanates or a mixture of two or more different tetraalkoxyzirconates or a mixture of at least one tetraalkoxysilane and at least one tetraalkoxytitanate or of at least one tetraalkoxysilane and at least one tetraalkoxyzirconate or of at least one tetraalkoxytitanate and at least one tetraalkoxyzirconate or a mixture of at least one tetraalkoxysilane and at least one tetraalkoxytitanate and at least one tetraalkoxyzirconate. In the context of the present invention binders which either completely or partly comprise $SiO_2$, or which are a precursor of $SiO_2$, from which $SiO_2$ is formed, may be preferred. In this context, both colloidal silica and so-called "wet process" silica and so-called "dry process" silica can be used. Particularly preferably this silica is amorphous silica, the size of the silica particles being, for example, in the range of from 5 to 100 nm and the surface area of the silica particles being in the range of from 50 to 500 $m^2$/g. Colloidal silica, preferably as an alkaline and/or ammoniacal solution, more preferably as an ammoniacal solution, is commercially available, inter alia, for example as Ludox®, Syton®, Nalco® or Snowtex®, "Wet process" silica is commercially available, inter alia, for example as Hi-Sil®, Ultrasil®, Vulcasil®, Santocel®, Valron-Estersil®, Tokusil® or Nipsil®. "Dry process" silica is commercially available, inter alia, for example as Aerosil®, Reolosil®, Cab-O-Sil®, Fransil® or ArcSilica®. Inter alia, an ammoniacal solution of colloidal silica is preferred in the present invention.

Pore forming agents include, but are not limited to, polymers such as polymeric vinyl compounds, such as polyalkylene oxides like polyethylene oxides, polystyrene, polyacrylates, polymethacrylates, polyolefins, polyamides and polyesters, carbohydrates, such as cellulose or cellulose derivatives like methyl cellulose, or sugars or natural fibers. Further suitable pore forming agents may be, for example, pulp or graphite. If desired with regard to the pore characteristics be achieved, a mixture of two or more pore forming agents may be used. In a particularly preferred embodiment of the process according to the invention, the pore forming agents are removed by calcination according to (ix) and/or (xi).

As to the ratio of the amount of the tin-containing zeolitic material relative to the amount of binder used for preparing a molding, it generally can be freely chosen. Generally, the weight ratio of the tin-containing zeolitic material relative to binder is in the range of from 20:1 to 1:20, preferably from 10:1 to 1:10, more preferably from 1:1 to 1:10.

For preparing a molding based on the tin-containing zeolitic material, at last one pasting agent can be used to provide for an improved processability of the moldable mixture. Conceivable pasting agents are, among others, organic, in particular hydrophilic polymers, such as, for example, carbohydrates like cellulose, cellulose derivatives, such as, for example, methyl cellulose, and starch, such as, for example, potato starch, wallpaper plaster, polyacrylates, polymethacrylates, polyvinyl alcohol, polyvinylpyrrolidone, polyisobutene or polytetrahydrofuran. The use of water, alcohols or glycols or mixtures thereof, such as mixtures of water and alcohol, or water and glycol, such as for example water and methanol, or water and ethanol, or water and propanol, or water and propylenglycol, as pasting agents may be mentioned. Preferably, carbohydrates such as cellulose, cellulose derivatives, water and mixtures of two or more of these compounds, such as water and cellulose or water and cellulose derivatives are used as pasting agent. In a particularly preferred embodiment of the process according to the invention, the at least one pasting agent is removed by drying and/or calcination, as further described below.

As to the ratio of the amount of tin-containing zeolitic material relative to the amount of pasting agent used for preparing a molding, it generally can be freely chosen. Generally, the weight ratio of the tin-containing zeolitic material relative to binder is in the range of from 20:1 to 1:50, preferably from 10:1 to 1:40, more preferably from 1:1 to 1:30.

The moldings of the present invention may be shaped in (vii) in every conceivable geometry such as strands, for example having rectangular, triangular hexagonal, quadratic, oval, or circular cross-section, stars, tablets, spheres, hollow cylinders, and the like. Depending on the specific geometry, the shaping process according to (vii) will be chosen. If, according to a preferred embodiment of the present invention, strands are prepared, the shaping according to (vii) preferably comprises extrusion. Suitable extrusion apparatuses are described, for example, in "Ullmann's Enzyklopädie der Technischen Chemie", 4th edition, vol. 2, page 295 et seq., 1972. In addition to the use of an extruder, an extrusion press can also be used for the preparation of the moldings. If necessary, the extruder can be suitably cooled during the extrusion process. Extrusion processes are conceivable wherein per batch, the power consumption is in the range of from 1 to 10 A, preferably from 1.5 to 6 A, more preferably from 2 to 4 A. The strands leaving the extruder via the extruder die head can be mechanically cut by a suitable wire or via a discontinuous gas stream.

The molding obtained from (vii) is optionally dried and/or calcined. No specific restrictions exist concerning the drying and calcination conditions. The drying is preferably carried out at temperatures in the range of in general from 75 to 200° C., preferably from 90 to 170° C., more preferably from 100 to 150° C., and preferably for a duration in the range of from 6 to 24 h, more preferably from 10 to 20 h. The drying can be effected under any suitable gas atmosphere, wherein nitrogen, air and/or lean air are preferred.

The calcination is preferably carried out at temperatures in the range of in general from 400 to 650° C., preferably from 450 to 600° C., more preferably from 475 to to 550° C., and preferably for a duration in the range of from 0.25 to 6 h, more preferably from 0.5 to 2 h. The calcination can be effected under any suitable gas atmosphere, wherein air and/or lean air are preferred.

Further, it is conceivable that the moldings comprising the tin-containing zeolitic material are subjected to a treatment with an aqueous system which has a pH in the range of 5.5 to 8.

Preferably, the moldings are treated with the aqueous system at a temperature in the range of from 80 to 220° C., preferably from 90 to 210° C., more preferably from 100 to 200° C. Further, the treating with the aqueous system is preferably carried out for a period in the range of from 1 to 20 h, more preferably from 4 to 15 h, more preferably from 6 to 10 h. Preferably, at least 95 weight-%, more preferably at least 99 weight-%, more preferably at least 99.9 weight-% of the aqueous system consists of water. More preferably, the aqueous system is water.

Preferably, the treating with the aqueous system is carried out in a closed system, under autogenous pressure and with or without stirring. According to another embodiment of the present invention, the treating with the aqueous system is carried out in an open system, preferably under reflux, and with or without stirring.

After treating of the moldings with the aqueous system, the moldings are preferably suitably separated from the suspension. All methods of separating the moldings from the suspension are conceivable. These methods include, for example, filtration and centrifugation methods. A combination of two or more of these methods can be applied. According to the present invention, the moldings are preferably separated from the aqueous system by filtration, and the thus obtained moldings are preferably subjected to washing, preferably to washing with water, at a temperature in the range of from up to 50° C., preferably from 15 to 35° C., more preferably from 20 to 30° C.

After treating with the aqueous system, the moldings are preferably subjected to drying and/or calcination, wherein drying is preferably carried out at a temperature in the range of from 100 to 180° C., preferably from 130 to 150° C., for a period in the range of from 10 to 70 h, preferably from 15 to 25 h, and calcination is preferably carried out at a temperature in the range of from 550° C. to 700° C., preferably from 600 to 680° C., for a period in the range of from 1 to 10 h, preferably from 2 to 5 h.

Generally, the present invention further relates to a zeolitic material, optionally contained in a molding, obtainable or obtained by a process according to the present invention.

Further, the present invention relates to a molding, comprising the zeolitic material of the present invention or the zeolitic material obtainable or obtained by the process of the present invention, said molding optionally additionally comprising a binder.

Therefore, the present invention also relates to the process above, further comprising (vii) shaping the tin-containing zeolitic material having an MWW-type framework structure obtained from (v) or (vi), preferably from (vi), obtaining a molding;
(viii) drying and/or calcining the molding obtained from (vii);
(ix) optionally subjecting the molding obtained from (vii) or (viii), preferably from (viii), to a water-treatment, wherein the water-treatment comprises treating the molding with liquid water in an autoclave under autogenous pressure at a temperature in the range of from 100 to 200° C.;
(x) optionally drying and/or calcining the water-treated molding obtained from (ix).

Therefore, the present invention also relates to the tin-containing zeolitic material having an MWW-type framework structure as described above, comprised in a molding, said molding preferably additionally comprising a binder, preferably a silica binder. Further, the present invention also relates to a molding comprising the tin-containing zeolitic material having an MWW-type framework structure as described above the molding optionally comprising at least one binder, preferably a silica binder. Yet further, the present invention relates to the use of the molding as a catalyst, preferably in oxidation reactions, preferably in BaeyerVilliger-type oxidation reactions, more preferably for the BaeyerVilliger oxidation of cyclic ketones, or in isomerization reactions, preferably for the isomerization of alpha-pinene oxide to campholenic aldehyde. Also, the present invention relates to an oxidation reaction, preferably a BaeyerVilliger-type oxidation reaction, more preferably the BaeyerVilliger oxidation of a cyclic ketone, or to an isomerization reactions preferably the isomerization of alpha-pinene oxide to campholenic aldehyde, wherein the molding as described above, comprising the tin-containing zeolitic material having an MWW-type framework structure as described above, is employed as a catalyst.

The present invention is further illustrated by the following Examples and Comparative Examples.

EXAMPLES

Reference Example 1: Determination of the Crystallinity

The crystallinity of the zeolitic materials according to the present invention was determined by XRD analysis. The data are collected using a standard Bragg-Brentano diffractometer with a Cu-X-ray source and an energy dispersive point detector. The angular range of 2° to 70° (2 theta) is scanned with a step size of 0.02°, while the variable divergence slit is set to a constant illuminated sample length of 20 mm. The data are then analyzed using TOPAS V4 software, wherein the sharp diffraction peaks are modeled using a Pawley fit containing a unit cell with the following starting parameters: a=14.4 Angstrom and c=25.2 Angstrom in the space group P6/mmm. These are refined to fit the data. Independent peaks are inserted at the following positions. 8.4°, 22.4°, 28.2° and 43°. A linear background is modelled. These are used to describe the amorphous content. The crystalline content describes the intensity of the crystalline signal to the intensity associated to the amorphous content.

Reference Example 2: Preparation of a Zeolitic Material Having an MWW-Type Framework Structure and Vacant Tetrahedral Sites 2.1 Preparation of a Boron-Containing Zeolitic Material Having an MWW-Type Framework Structure (B-MWW)

480 kg de-ionized water were provided in a vessel. Under stirring at 70 rpm (rounds per minute), 166 kg boric acid were suspended in the water at room temperature. The suspension was stirred for another 3 h at room temperature. Subsequently, 278 kg piperidine were added, and the mixture was stirred for another hour. To the resulting solution, 400 kg Ludox® AS-40 were added, and the resulting mixture was stirred at 70 rpm for another hour at room temperature. The finally obtained mixture was transferred to a crystallization vessel and heated to 170° C. within 5 h under autogenous pressure and under stirring (50 r.p.m.). The temperature of 170° C. was kept essentially constant for 120 h. During these 120 h, the mixture was stirred at 50 rpm. Subsequently, the mixture was cooled to a temperature of from 50-60° C. The aqueous suspension containing B-MWW precursor had a pH of 11.3 as determined via measurement with a pH-sensitive electrode. From said suspension, the B-MWW precursor was separated by filtration. The filter cake was then washed with de-ionized water at room temperature until the washing water had a conductivity of less than 500 microSiemens/cm. The thus obtained filter cake, after having prepared an aqueous suspension thereof having a solids content if 15 weight-% based on the total weight of the suspension, was subjected to spray-drying in a spray-tower with the following spray-drying conditions:
drying gas, nozzle gas: technical nitrogen
temperature drying gas:
    temperature spray tower (in): 235° C.
    temperature spray tower (out): 140° C. nozzle:
    top-component nozzle supplier Gerig; size 0
    nozzle gas temperature: room temperature
    nozzle gas pressure: 1 bar
operation mode: nitrogen straight
apparatus used: spray tower with one nozzle
configuration: spray tower-filter-scrubber
gas flow: 1,500 kg/h
filter material: Nomex® needle-felt 20 m²
dosage via flexible tube pump: SP VF 15 (supplier: Verder)

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening.

The spray-dried material was then subjected to calcination at 650° C. in a rotary oven in countercurrent flow (0.8-1 kg/h). The calcined B-MWW material had a B content of 1.4 weight-%, a Si content of 43 weight-%, and a TOC (total organic carbon) of less than 0.1 weight-%. The crystallinity of the material, as determined via XRD, was 88%, and the BET specific surface area measured according to DIN 66131 was 468 m²/g.

2.2 Deboronation—Forming Vacant Tetrahedral Sites 1590 kg of de-ionized water and 106 kg of the calcined material obtained according 2.1 above were refluxed at 100° C. under stirring at 70 r.p.m. for 10 h. The resulting deboronated zeolitic material was separated from the suspension by filtration and washed 4 times with 150 l deionized water at room temperature. After the filtration, the filter cake was dried at a temperature of 120° C. for 16 h.

The dried zeolitic material having an MWW-type framework structure had a B content of 0.04 weight-%, a Si content of 42 weight-%, a crystallinity determined via XRD of 82% and a BET specific surface area of 462 m²/g.

Example 1: Preparation of a Tin-Containing Zeolitic Material Having an MWW-Type Framework Structure 30 g of the deboronated zeolitic material obtained according to Reference Example 2 were added in a Mixer (mill type Microton MB550) together with 8.9 g Sn(OAc)$_2$ (tin(II) acetate, CAS-Nr:638-39-1, Sigma-Aldrich). The two components were milled together for 15 minutes with a stirring rate of 14,000 r.p.m. (rounds per minute). Afterwards, 10.8 g of the thus obtained powder were transferred to a porcelain holder and calcined in a static oven for 5 h at 550° C., heating rate 2 K/min. The calcined powder had the following elemental composition: Sn 12.0 weight-%, Si 35.5 weight-% and TOC of less than 0.1 weight-%. The BET specific surface area determined according to DIN 66131 was 383 m²/g, and the crystallinity determined via XRD was 75%.

330 g of nitric acid (30 weight-%) and 11 g of the calcined zeolitic material were added under stirring in a 0.5 l glass round bottom flask. The mixture in the vessel was heated to 100° C. and kept at this temperature under autogenous pressure for 20 h under stirring (200 r.p.m.). The thus obtained mixture was then cooled within 1 h to a temperature of less than 50° C.

The cooled mixture was subjected to filtration, and the filter cake was washed with de-ionized water until a pH of 7 was reached. The filter cake was dried for 10 h at 120° C. and calcined at 550° C. for 10 h (heating ramp 2 K/min). A zeolitic material was obtained having a Sn content of 12.6 weight-%, a Si content of 36.5 weight-% and a TOC of less than 0.1 weight-%. The BET specific surface area determined according to DIN 66131 was 385 m²/g, and the crystallinity was 80%.

Example 2: Preparation of a Tin-Containing Zeolitic Material Having an MWW-Type Framework Structure 30 g of the deboronated zeolitic material obtained according to Reference Example 2 were added in a Mixer (mill type Microton MB550) together with 8.9 g Sn(OAc)$_2$ (tin(II) acetate, CAS-Nr:638-39-1, Sigma-Aldrich). The two components were milled together for 15 minutes with a stirring rate of 14,000 r.p.m. (rounds per minute). Afterwards, 10.8 g of the thus obtained powder were transferred to a porcelain holder and dried at 120° C. for 10 h.

285 g of nitric acid (30 weight-%) and 9.5 g of the dried zeolitic material were added under stirring in a 0.5 l glass round bottom flask. The mixture in the vessel was heated to 100° C. and kept at this temperature under autogenous pressure for 20 h under stirring (200 r.p.m.). The thus obtained mixture was than cooled within 1 h to a temperature of less than 50° C.

The cooled mixture was subjected to filtration, and the filter cake was washed with de-ionized water until a pH of 7 was reached. The filter cake was dried for 10 h at 120° C. and calcined at 550° C. for 10 h (heating ramp 2 K/min). A zeolitic material was obtained having a Sn content of 12.8 weight-%, a Si content of 37 weight-% and a TOC of less than 0.1 weight-%. The BET specific surface area determined according to DIN 66131 was 391 m²/g, and the crystallinity determined via XRD was 87%.

Example 3: Preparation of a Tin-Containing Zeolitic Material Having an MWW-Type Framework Structure 120 g of the deboronated zeolitic material obtained according to Reference Example 2 were added in a Mixer (mill type Microton MB550) together with 34 g Sn(OAc)$_2$ (tin(II) acetate, CAS-Nr:638-39-1, Sigma-Aldrich). The two components were milled together for 15 minutes with a stirring rate of 14,000 r.p.m. (rounds per minute). Afterwards, 28 g of the thus obtained powder were transferred to a porcelain holder and calcined in a static oven for 3 h at 500° C., heating rate 2 K/min. The calcined powder had the following elemental composition: Sn 11.5 weight-%, Si 35 weight-% and TOC of less than 0.1 weight-%. The BET specific surface area determined according to DIN 66131 was 392 m$^2$/g, and the crystallinity determined via XRD was 79%. The XRD spectrum of the zeolitic material is shown in FIG. 1.

1800 g of nitric acid (30 weight-%) and 60 g of the calcined zeolitic material were added under stirring in a 2.0 l glass round bottom flask. The mixture in the vessel was heated to 100° C. and kept at this temperature under autogenous pressure for 20 h under stirring (200 r.p.m.). The thus obtained mixture was then cooled within 1 h to a temperature of less than 50° C.

Figure 2:
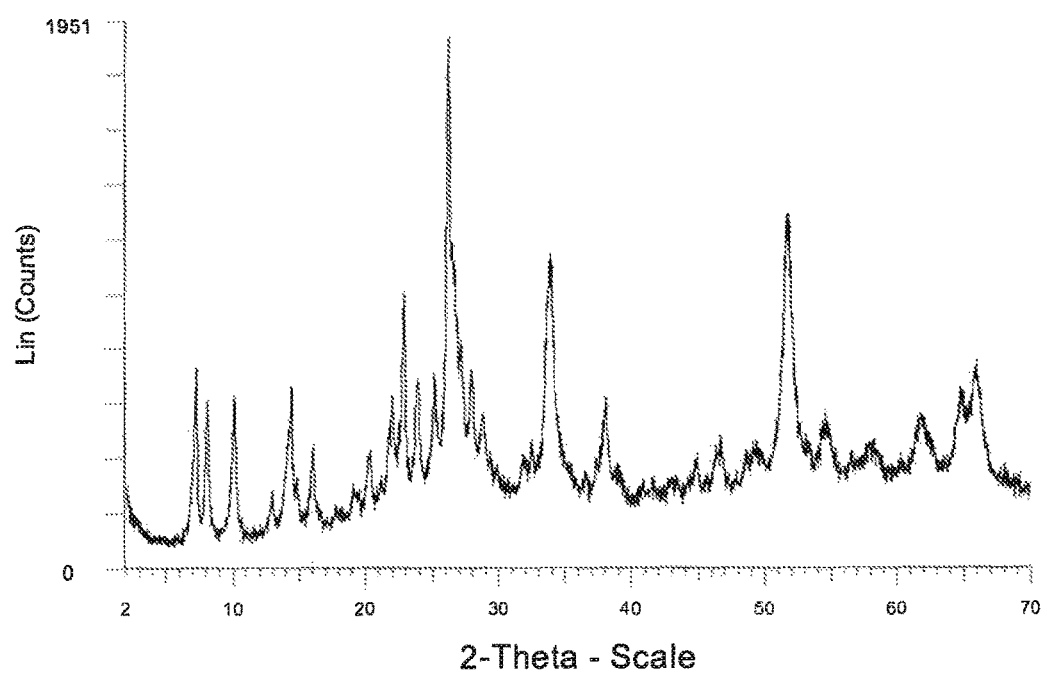
FIG. 2 shows the X-ray diffraction pattern (copper K alpha radiation) of the acid treated zeolitic material obtained according to Example 3. On the x axis, the degree values (2 Theta) are shown, on the y axis, the intensity (Lin (Counts)). Tick mark labels on the x axis are, from left to right, 2, 10, 20, 30, 40, 50, 60, 70. Tick mark labels on the y axis are 0 and 1951.

The cooled mixture was subjected to filtration, and the filter cake was washed with de-ionized water until a pH of 7 was reached. The filter cake was dried for 10 h at 120° C. and calcined at 550° C. for 5 h (heating ramp 2 K/min). A material with a Sn content of 12.3 weight-%, a Si content of 37 weight-%, and a TOC of less than 0.1 weight-% was obtained. The BET specific surface area determined according to DIN 66131 was 400 m$^2$/g, and the crystallinity determined via XRD was 84%. The XRD spectrum of the zeolitic material is shown in FIG. 2.

Comparative Example 1: Preparation of a Tin-Containing Zeolitic Material Having an MWW-Type Framework Structure by Hydrothermal Synthesis 1.1 Preparation of a Boron-Containing Zeolitic Material Having an MWW-Type Framework Structure 480 kg de-ionized water were provided in a vessel. Under stirring at 70 rpm (rounds per minute), 166 kg boric acid were suspended in the water at room temperature. The suspension was stirred for another 3 h at room temperature. Subsequently, 278 kg piperidine were added, and the mixture was stirred for another hour. To the resulting solution, 400 kg Ludox® AS-40 were added, and the resulting mixture was stirred at 70 rpm for another hour at room temperature. The finally obtained mixture was transferred to a crystallization vessel and heated to 170° C. within 5 h under autogenous pressure and under stirring (50 rpm). The temperature of 170° C. was kept essentially constant for 120 h. During these 120 h, the mixture was stirred at 50 rpm. Subsequently, the mixture was cooled to a temperature of from 50-60° C. The aqueous suspension containing B-MWW precursor had a pH of 11.3 as determined via measurement with a pH-sensitive electrode. From said suspension, the B-MWW precursor was separated by filtration. The filter cake was then washed with de-ionized water at room temperature until the washing water had a conductivity of less than 700 microSiemens/cm. The thus obtained filter cake, after having prepared an aqueous suspension thereof having a solids content if 15 weight-% based on the total weight of the suspension, was subjected to spray-drying in a spray-tower with the following spray-drying conditions:
drying gas, nozzle gas: technical nitrogen
temperature drying gas:
    temperature spray tower (in): 235° C.
    temperature spray tower (out): 140° C. nozzle:
    top-component nozzle supplier Gerig; size 0
    nozzle gas temperature: room temperature
    nozzle gas pressure: 1 bar
operation mode: nitrogen straight
apparatus used: spray tower with one nozzle
configuration: spray tower-filter-scrubber
gas flow: 1,500 kg/h
filter material: Nomex® needle-felt 20 m$^2$
dosage via flexible tube pump: SP VF 15 (supplier: Verder)

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening.

The spray-dried material was then subjected to calcination at 600° C. for 10 h. The calcined material had a molar ratio B$_2$O$_3$:SiO$_2$ of 0.06:1.

1.2 Deboronation—Forming Vacant Tetrahedral Sites 9 kg of de-ionized water and 600 g of the calcined zeolitic material obtained according to Example 1 (i) were refluxed at 100° C. under stirring at 250 r.p.m. for 10 h. The resulting deboronated zeolitic material was separated from the suspension by filtration and washed with 4 l deionized water at room temperature. After the filtration, the filter cake was dried at a temperature of 120° C. for 16 h.

The dried zeolitic material having an MWW framework structure had a B$_2$O$_3$:SiO$_2$ molar ratio of 0.0020:1.

1.3 Incorporation of Sn Via Hydrothermal Treatment 776.25 g deionized water were provided in a glass beaker and 375 g piperidine were added under stirring. To this suspension 2.9 g of tin(II) acetate were added and the suspension was stirred for another 10 min. 172.4 g deboronated zeolitic material obtained according to 2.2 were added to the mixture, and the resulting mixture was stirred for 20 min (200 r.p.m.) at room temperature. The obtained suspension was then filled in an autoclave. The mixture was treated for 48 h at a temperature of 170° C. under stirring (100 r.p.m.). Afterwards the autoclave was cooled down to room temperature and the resulting zeolitic material was separated from the suspension by filtration at room temperature and washed with deionized water until the washing water had a conductivity of less than 200 microSiemens/cm. After the filtration, the filter cake was dried at a temperature of 120° C. for 16 h.

The dried zeolitic material had a Si content of 39 weight-% and a Sn content of 1.0 weight-%.

1.4 Acid Treatment 50 g zeolitic material obtained according 2.3 were provided in a round bottom flask, and 1500 g of a 30 weight-% HNO$_3$ aqueous solution, having a pH in the range of from 0 to 1, were added. The mixture was stirred at a temperature of 100° C. for a period of 20 h (200 r.p.m.). The suspension was filtered and the filter cake was than washed with de-ionized water at room temperature until the washing water had a pH of approximately 7. The obtained zeolitic material was dried at 120° C. for 16 h and calcined by heating to 550° C. (2 K/min) and subsequent heating at 550° C. for 10 h.

The dried and calcined zeolitic material had a Si content of 47 weight-% and a Sn content of 1.1 weight-% and a c parameter as determined via XRD of 26.4 Angstrom. Further, the zeolitic material had a BET surface area, determined according to DIN 66131 of 456 m²/g.

Example 4: Use of the Tin-Containing Zeolitic Material According to Example 2 and Comparative Example 1

Isomerization of Alpha-Pinene Oxide to Campholenic Aldehyde

The zeolitic powders as prepared according to Example 2 and Comparative Example 1 were used as catalysts in the isomerization reaction of alpha-pinene oxide to campholenic aldehyde:

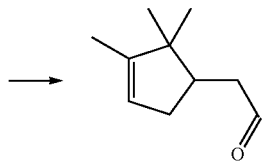

The isomerization reaction was carried out as a batch reaction according to which 0.48 g alpha-pinene oxide and 0.02 g of the respective tin-containing zeolitic material were brought together in 5 ml 1,4-dioxane. This mixture was then stirred at 75° C. for 3 h. Then, the catalyst was separated by filtration. The filtrate was analysed using a calibrated GC/MS (biphenyl as internal standard) and NMR. The analytical data are as follows:

¹H-NMR: 0.8 (s, 3H); 1.01 (s, 3H); 1.63 (s, 3H); 1.90 (m, 1H); 2.3 (m, 1H); 2.4 (m, 2H); 2.53 (m, 1H); 5.24 (s, 1H); 9.8 (2, J=2, 1 H).
¹³C-NMR: 12.5 (q) 20.2 (q), 25.6 (q) 35.6 (t), 44.3 (d), 45.1 (t), 46.9 (s), 121.7 (d), 147.8 (s), 202.1 (d).
MS: 152 (2 μM⁺), 137 (3), 119 (5), 108 (100), 105 (10), 93 (62), 67 (27), 41 (20).

The results of the experiments are shown in the following Table 1,

TABLE 1

Results of Example 4

| Catalyst of | Conversion of alpha-pinene oxide/% | Selectivity to campholenic aldehyde based on alpha-pinene oxide/% |
|---|---|---|
| Example 2 | >99 | 81 |
| Comparative Example 1 | 88 | 69 |

These results clearly show that the catalyst according to the present invention exhibits by far the best conversion and selectivity values.

SHORT DESCRIPTION OF THE FIGURES

FIG. 1 shows the X-ray diffraction pattern (copper K alpha radiation) of the non-acid treated zeolitic material obtained according to Example 3. On then axis, the degree values (2 Theta) are shown, on the y axis, the intensity (Lin (Counts)). Tick mark labels on the x axis are, from left to right, 2, 10, 20, 30, 40, 50, 60, 70. Tick mark labels on the y axis are 0 and 1951.

FIG. 2 shows the X-ray diffraction pattern (copper K alpha radiation) of the acid treated zeolitic material obtained according to Example 3. On the x axis, the degree values (2 Theta) are shown, on the y axis, the intensity (Lin (Counts)). Tick mark labels on the x axis are, from left to right, 2, 10, 20, 30, 40, 50, 60, 70. Tick mark labels on the y axis are 0 and 1951.

CITED LITERATURE

WO 03/074422 A1
U.S. Pat. No. 7,326,401 B2
Microporous and Mesoporous Materials 165 (2013), pages 210-218
M. A. Camblor, A. Corma, M.-J. Diaz-Cabanas and Ch. Baerlocher, J. Phys. Chem. B 102 44-51 (1998)

The invention claimed is:

1. A process for preparing a tin-containing zeolitic material having an MWW-type framework structure, the process comprising
   (i) providing a zeolitic material having an MWW-type framework structure comprising $X_2O_3$ and $YO_2$, wherein Y is a tetravalent element selected from the group consisting of Si, Ti, Zr, Ge, and combinations of two or more thereof, and X is a trivalent element selected from the group consisting of Al, B, In, Ga, Fe, and combinations of two or more thereof, said MWW-type framework structure having vacant tetrahedral framework sites;
   (ii) providing a tin-ion source in solid form;
   (iii) incorporating tin into the zeolitic material provided in (i) by contacting the zeolitic material provided in (i) with the tin-ion source provided in (ii) under solid-state ion exchange conditions, to provide a tin-containing zeolitic material having an MWW-type framework structure.

2. The process of claim 1, wherein Y is Si and X is B.

3. The process of claim 1, wherein according to (i), the zeolitic material having an MWW-type framework structure having vacant tetrahedral framework sites is provided by a method comprising
   (i.1) providing a zeolitic starting material having an MWW-type framework structure, wherein the framework structure of the zeolitic starting material comprises $X_2O_3$ and $YO_2$ and the molar ratio $X_2O_3:YO_2$ is at least 0.03:1;
   (i.2) creating vacant tetrahedral framework sites by treating the zeolitic starting material provided in (i.1) with a liquid solvent system, to provide a zeolitic material having a molar ratio $X_2O_3:YO_2$ of less than 0.03:1, wherein the liquid solvent system is selected from the group consisting of water, methanol, ethanol, propanol, ethane-1,2-diol, propane-1,2-diol, propane-1,3-diol, propane-1,2,3-triol, and mixtures of two or more thereof, wherein the treating is carried out at a temperature in a range of from 50 to 125° C., and for a period in a range of from 6 to 20 h;
   (i.3) at least partially separating the zeolitic material obtained from (i.2) from the liquid solvent system, optionally including drying carried out at a temperature in a range of from 100 to 180° C.;
   (i.4) optionally calcining the separated zeolitic material obtained from (i.3) at a temperature in a range of from 400 to 800° C.

4. The process of claim 1, wherein in the framework structure of the zeolitic material provided in (i), the molar ratio $X_2O_3:YO_2$ is at most 0.01:1.

5. The process of claim 1, wherein at least 95 weight-% of the framework structure of the zeolitic material provided in (i) consist of $X_2O_3$ and $YO_2$.

6. The process of claim 1, wherein the tin-ion source provided in (ii) is selected from the group consisting of tin(II) alkoxides, tin(IV) alkoxides, tin(II) salts of organic acids, tin(IV) salts of organic acids, and a mixture a two or more thereof.

7. The process of claim 6, wherein the tin(II) alkoxides have from 1 to 4 carbon atoms, the tin(IV) alkoxides have from 1 to 4 carbon atoms, the tin(II) salts of organic acids have from 1 to 6, the tin(IV) salts of organic acids have from 1 to 6 carbon atoms.

8. The process of claim 1, wherein according to (iii), the molar ratio of tin contained in the tin-ion source brought into contact with zeolitic material relative to the vacant tetrahedral framework sites of the zeolitic material is at most 1:1.

9. The process of claim 1, wherein in (iii), bringing the zeolitic material provided in (i) in contact with the tin-ion source provided in (ii) under solid-state ion exchange conditions comprises mixing the zeolitic material provided in (i) together with the tin-ion source.

10. The process of claim 9, wherein in (iii), the zeolitic material is mixed with the tin-ion source for a time period in the range of from 2 min to 5 h.

11. The process of claim 9, wherein the mixing is carried out under stirring at a stirring energy input min the range of from 100 to 1000 W.

12. The process of claim 11, comprising grinding and/or milling the zeolitic material prior to mixing the zeolitic material together with the tin-ion source, or grinding and/or milling the tin-ion source prior to mixing the zeolitic material together with the tin-ion source, or grinding and/or milling the zeolitic material prior to mixing the zeolitic material together with the tin-ion source and grinding and/or milling the tin-ion source prior to mixing the zeolitic material together with the tin-ion source.

13. The process of claim 1, further comprising
(iv) subjecting the zeolitic material obtained from (iii) to a heat-treatment.

14. The process of claim 13, wherein the heat-treating according to (iv) comprises drying and the drying is carried out at a temperature in a range of from 75 to 175° C., for a time period in a range of from 2 to 48 h at least partially in an atmosphere comprising oxygen.

15. The process of claim 13, wherein the heat-treating according to (iv) comprises calcining and the calcining is carried out at a temperature in a range of from 400 to 700° C., for a time period in a range of from 1 to 10 h, at least partially in an atmosphere comprising oxygen.

16. The process of claim 13, further comprising
(v) treating the zeolitic material obtained from (iii) or (iv), with an aqueous solution having a pH of at most 5.

17. The process of claim 16, wherein in (v), the aqueous solution comprises an organic acid selected from the group consisting of oxalic acid, acetic acid, citric acid, methane sulfonic acid, and a mixture of two or more thereof, and/or comprises an inorganic acid selected from the group consisting of phosphoric acid, sulphuric acid, hydrochloric acid, nitric acid, and a mixture of two or more thereof.

18. The process of claim 16, wherein in (v), the aqueous solution has a pH in a range of from 0 to 3.5.

19. The process of claim 18, wherein in (v), the zeolitic material is treated with the aqueous solution at a temperature in a range of from 70° C. to 100° C. in a closed system under autogenous pressure.

20. The process of claim 19, wherein in (v), the zeolitic material is treated with the aqueous solution for a time period in a range of from 10 min to 40 h.

21. The process of claim 19, wherein in (v), the zeolitic material is treated with the aqueous solution at a weight ratio of the aqueous solution relative to the zeolitic material in a range of from 2:1 to 50:1.

22. The process of claim 19, further comprising
(vi) drying and calcining the zeolitic material obtained (v), wherein the drying is preferably carried out at a temperature in the range of from 90° C. to 180° C., for a period in a range of from 1 h to 24 h, and the calcining is carried out at a temperature in the range of from 400 to 700° C., for a period in a range of from 1 h to 24 h.

23. The process of claim 22, further comprising
(vii) shaping the tin-containing zeolitic material having an MWW-type framework structure obtained from (iii), (iv), (v) or (vi), with a binder or a precursor thereof, to provide a molding;
(viii) drying and/or calcining the molding obtained from (vii);
(ix) optionally subjecting the molding obtained from (vii) or (viii), to a water-treatment, wherein the water-treatment comprises treating the molding with liquid water in an autoclave under autogenous pressure at a temperature in a range of from 100 to 200° C.;
(x) optionally drying and/or calcining the water-treated molding obtained from (ix).

24. A tin-containing zeolitic material, obtained by a process according to claim 1, wherein the zeolitic material has a tin content of at least 10 weight-%.

25. A tin-containing zeolitic material having an MWW-type framework structure comprising $X_2O_3$ and $YO_2$, wherein Y is a tetravalent element selected from the group consisting of Si, Ti, Zr, Ge, and combinations of two or more thereof, X is a trivalent element selected from the group consisting of Al, B, In, Ga, Fe, and combinations of two or more thereof, wherein the framework structure additionally comprises tin, wherein in the framework structure of the zeolitic material, the molar ratio $X_2O_3:YO_2$ is in a range of from 0.001:1 to 0.01:1, wherein at least 98 weight-% of the framework structure of the zeolitic material consist of X, Y, O, and tin, and wherein the tin-containing zeolitic material has a tin content of at least 10 weight-%, based on the total weight of the tin-containing zeolitic material.

26. The tin-containing zeolitic material of claim 25, having a tin content in a range of from 11 to 18 weight-%, based on the total weight of the tin-containing zeolitic material.

27. The tin-containing zeolitic material of claim 26, obtained by a process comprising
(i) providing a zeolitic material having an MWW-type framework structure comprising $X_2O_3$ and $YO_2$, wherein Y is a tetravalent element selected from the group consisting of Si, Ti, Zr, Ge, and combinations of two or more thereof, and X is a trivalent element selected from the group consisting of Al, B, In, Ga, Fe, and combinations of two or more thereof, said MWW-type framework structure having vacant tetrahedral framework sites;
(ii) providing a tin-ion source in solid form;
(iii) incorporating tin into the zeolitic material provided in (i) by contacting the zeolitic material provided in (i) with the tin-ion source provided in (ii) under solid-state ion exchange conditions, to provide a tin-containing zeolitic material having an MWW-type framework structure.

28. A molding composition comprising the tin-containing zeolitic material of claim 26 and a silica binder.

29. A process of isomerizing alphia-pinene oxide to campholenic aldehyde comprising contacting the molding of claim 28 with alpha-pinene oxide under isomerization conditions.

\* \* \* \* \*